(12) United States Patent
Zeglis et al.

(10) Patent No.: US 11,000,604 B2
(45) Date of Patent: May 11, 2021

(54) REAGENT FOR SITE-SELECTIVE BIOCONJUGATION OF PROTEINS OR ANTIBODIES

(71) Applicant: Research Foundation of the City University of New York, New York, NY (US)

(72) Inventors: Brian Zeglis, New York, NY (US); Pierre Adumeau, New York, NY (US); Maria Davydova, New York, NY (US)

(73) Assignee: Research Foundation of the City University of New York, New York, NY (US)

(*) Notice: Subject to any disclaimer, the term of this patent is extended or adjusted under 35 U.S.C. 154(b) by 0 days.

(21) Appl. No.: 16/614,073

(22) PCT Filed: May 17, 2018

(86) PCT No.: PCT/US2018/033124
§ 371 (c)(1),
(2) Date: Nov. 15, 2019

(87) PCT Pub. No.: WO2018/213537
PCT Pub. Date: Nov. 22, 2018

(65) Prior Publication Data
US 2020/0397928 A1 Dec. 24, 2020

Related U.S. Application Data

(60) Provisional application No. 62/634,385, filed on Feb. 23, 2018, provisional application No. 62/507,477, filed on May 17, 2017.

(51) Int. Cl.
*A61K 51/10* (2006.01)
*A61K 47/68* (2017.01)
*C07D 271/113* (2006.01)

(52) U.S. Cl.
CPC ...... *A61K 51/1063* (2013.01); *A61K 47/6863* (2017.08); *A61K 47/6889* (2017.08); *C07D 271/113* (2013.01)

(58) Field of Classification Search
None
See application file for complete search history.

(56) References Cited

U.S. PATENT DOCUMENTS

2014/0249296 A1 9/2014 Ploegh et al.

FOREIGN PATENT DOCUMENTS

WO WO2014144878 9/2014

OTHER PUBLICATIONS

Toda et al. (Angewandte Int. Ed. Chemi, 52(48): 12592-12596, 2013).*

Adumeau, P. et al.; Thiol-Reactive Bifunctional Chelators for the Creation of Site-Selectively Modified Radioimmunoconjugates with Improved Stability; Bioconjugate Chem.; Mar. 6, 2018; pp. 1364-1372; vol. 29; https://doi.org/10.1021/acs.bioconjchem.8b00081.
Adumeau, P. et al.; Site-Specifically Labeled Immunoconjugates for Molecular Imaging—Part 1: Cysteine Residues and Glycans; Mol Imaging Biol.; Jan. 11, 2016; pp. 1-17; vol. 18, No. 1.
ISA/US; International Search Report/Written Opinion dated Jul. 13, 2018 for corresponding International application PCT/US18/33124.
Alley, S. et al.; Contribution of Linker Stability to the Activities of Anticancer Immunoconjugates; Bioconjugate Chem.; Mar. 4, 2008; pp. 759-765; vol. 19.
Baldwin, A. et al.; Tunable Degradation of Maleimide-Thiol Adducts in Reducing Environments; Bioconjugate Chem.; Aug. 25, 2011; pp. 1946-1953; vol. 22; dx.doi.org/10.1021/bc200148v.
Banerjee, S.; Lutetium-177 Therapeutic Radiopharmaceuticals: Linking Chemistry, Radiochemistry, and Practical Applications; Chemical Reviews; Apr. 13, 2015; pp. 2934-2974; vol. 115; DOI: 10.1021/cr500171e.
Behrens, C. et al.; Methods for site-specific drug conjugation to antibodies; mAbs; Jan.-Feb. 2014; pp. 46-53; 6:1;.
Agarwal, P. et al.; Site-Specific Antibody-Drug Conjugates: The Nexus of Bioorthogonal Chemistry, Protein Engineering, and Drug Development; Bioconjugate Chem.; Dec. 12, 2014; pp. 176-192; vol. 26; DOI: 10.1021/bc5004982.
Chiotellis, A. et al; Novel chemoselective 18F-radiolabeling of thiol-containing biomolecules under mild aqueous conditions; ChemComm; Mar. 30, 2016; pp. 6083-6086; vol. 52; DOI: 10.1039/c6cc01982j.
Deri, M. et al.; PET imaging with 89Zr: From radiochemistry to the clinic; Nuclear Medicine and Biology; 2013; pp. 3-14; vol. 40.
Dozier, J. et al,; Site-Specific PEGylation of Therapeutic Proteins; Int. J. Mol. Sci.; Oct. 28, 2015; pp. 25832-25864; vol. 16; doi:10.3390/ijms161025831.
Freidel, C. et al.; Chemical tags for site-specific fluorescent labeling of biomolecules; Amino Acids; Mar. 11, 2016; pp. 1357-1372; vol. 48; DOI 10.1007/s00726-016-2204-5.
Jackson, D. et al.; In Vitro and In Vivo Evaluation of Cysteine and Site Specific Conjugated Herceptin Antibody-Drug Conjugates; PLOS; Jan. 14, 2014; pp. 1-14; vol. 9 | Issue 1.
Jauw, Y. et al.; Immuno-Positron Emission Tomography with Zirconium-89-Labeled Monoclonal Antibodies in Oncology: What Can We Learn from Initial Clinical Trials?; FrontiersinPharmacology; May 24, 2016; pp. 1-15; vol. 7 | Article131; doi: 10.3389/fphar.2016.00131.

(Continued)

*Primary Examiner* — Nelson B Moseley, II
(74) *Attorney, Agent, or Firm* — Peter J. Mikesell; Schmeiser, Olsen & Watts, LLP

(57) ABSTRACT

A label for an antibody or protein is described that is both site-selective and unusually stable in vivo. The label has a general formula given by Formula (I) wherein $R_1$ is a metal chelator, a fluorophore or a click-chemistry synthon.

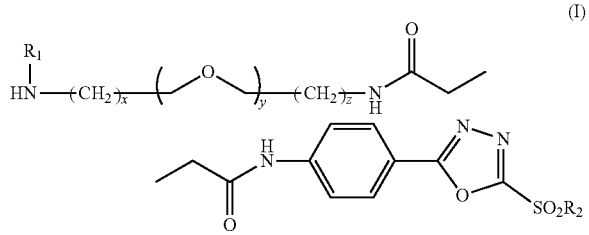

20 Claims, 10 Drawing Sheets

(56) References Cited

OTHER PUBLICATIONS

Khalili, H. et al.; Comparative Binding of Disulfide-Bridged PEG-Fabs; Bioconjugate Chem.; Sep. 21, 2012; pp. 2262-2277; vol. 23; dx.doi.org/10.1021/bc300372r.

Koniev, O. et al.; Developments and recent advancements in the field of endogenous amino acid selective bond forming reactions for bioconjugation; Chem. Soc. Rev.; 2015; pp. 5495-5551; vol. 44; DOI: 10.1039/c5cs00048c.

Li, L. et al.; Site-Specific Conjugation of Monodispersed DOTA-PEGn to a Thiolated Diabody Reveals the Effect of Increasing PEG Size on Kidney Clearance and Tumor Uptake with Improved 64-Copper PET Imaging; Bioconjugate Chem.; Mar. 12, 2011; pp. 709-716; vol. 22; dx.doi.org/10.1021/bc100464e l.

Li, L. et al.; Reduction of Kidney Uptake in Radiometal Labeled Peptide Linkers Conjugated to Recombinant Antibody Fragments. Site-Specific Conjugation of DOTA-Peptides to a Cys-Diabody; Bioconjugate Chem.; Aug. 28, 2002; pp. 985-995; vol. 13.

Li, X. et al.; Site-Specific Dual Antibody Conjugation via Engineered Cysteine and Selenocysteine Residues; Bioconjugate Chem.; Jul. 10, 2015; pp. 2243-2248; vol. 26.; DOI: 10.1021/acs.bioconjchem. 5b00244.

Patterson, J. et al.; Improving the Serum Stability of Site-Specific Antibody Conjugates with Sulfone Linkers; Bioconjugate Chem.; Aug. 6, 2014; pp. 1402-1407; vol. 25; dx.doi.org/10.1021/bc500276m.

Ponte, J. et al.; Understanding How the Stability of the Thiol-Maleimide Linkage Impacts the Pharmacokinetics of Lysine-Linked Antibody-Maytansinoid Conjugates; Bioconjugate Chem.; May 13, 2016; pp. 1588-1598; vol. 27; DOI: 10.1021/acs.bioconjchem. 6b00117.

Shen, B. et al.; Conjugation site modulates the in vivo stability and therapeutic activity of antibody-drug conjugates; nature biotechnology; Jan. 22, 2012; pp. 184-191; vol. 30, No. 2; doi:10.1038/nbt. 2108.

Stimmel, J. et al.; Site-specific Conjugation on Serine—> Cysteine Variant Monoclonal Antibodies; The Journal of Biological Chemistry; Jul. 3, 2000; pp. 30445-30450; vol. 275, No. 39; DOI 10.1074/jbc.M001672200.

Tinianow, J. et al.; Site-specifically 89Zr-labeled monoclonal antibodies for ImmunoPET; Nuclear Medicine and Biology; 2010; pp. 289-297; vol. 37.

Toda, N. et al.; Rapid, Stable, Chemoselective Labeling of Thiols with Julia—Kocienski-like Reagents: A Serum-Stable Alternative to Maleimide-Based Protein Conjugation; Angew. Chem. Int. Ed.; 2013; pp. 12592-12596; vol. 52.

Verel, I. et al.; 89Zr Immuno-PET: Comprehensive Procedures for the Production of 89Zr-Labeled Monoclonal Antibodies; The Journal of Nuclear Medicine; Aug. 2003; pp. 1271-1281; vol. 44, No. 8.

Zhang, Q. et al.; Last-Step Enzymatic [18F]-Fluorination of Cysteine-Tethered RGD Peptides Using Modified Barbas Linkers; Chem. Eur. J.; 2016; pp. 10998-11004; vol. 22.

* cited by examiner

| Tumor : Organ | 89Zr-DFO-mal-huA33 | | | 89Zr-DFO-PODS-huA33 | | |
|---|---|---|---|---|---|---|
| | 24h | 48h | 120h | 24h | 48h | 120h |
| Blood | 4.4 ± 1.5 | 13.1 ± 4.9 | 25.1 ± 5.0 | 5.2 ± 2.8 | 11.9 ± 1.7 | 46.9 ± 29.6 |
| Heart | 10.1 ± 2.6 | 26.8 ± 6.8 | 33.3 ± 4.3 | 12.4 ± 6.3 | 25.9 ± 4.7 | 54.4 ± 18.5 |
| Lung | 8.5 ± 2.3 | 21.6 ± 6.5 | 28.9 ± 5.8 | 9.9 ± 4.9 | 20.0 ± 4.0 | 50 ± 26.4 |
| Liver | 9.3 ± 2.2 | 17.4 ± 4.9 | 13.6 ± 2.4 | 12.8 ± 5.9 | 28.8 ± 4.2 | 24.4 ± 8.5 |
| Spleen | 8.5 ± 4.9 | 20.9 ± 6.8 | 14.9 ± 1.6 | 15.6 ± 7.2 | 31.3 ± 4 | 23.2 ± 13.4 |
| Stomach | 37.7 ± 19.8 | 67.1 ± 17.5 | 90.8 ± 20.5 | 21.8 ± 10.4 | 45.4 ± 6.4 | 119.5 ± 39.6 |
| S. Intestine | 20.3 ± 10.3 | 45.0 ± 15.2 | 75.9 ± 9.3 | 22.1 ± 10.3 | 43.6 ± 7 | 86.6 ± 39.5 |
| L. Intestine | 53.9 ± 20.0 | 103.6 ± 32.3 | 131.6 ± 29.8 | 24.8 ± 14.2 | 46.5 ± 9.4 | 67.3 ± 17.9 |
| Kidney | 5.6 ± 1.2 | 10.8 ± 2.7 | 12.0 ± 2.3 | 11.7 ± 5.7 | 21.5 ± 2.7 | 19.4 ± 5.2 |
| Muscle | 30.0 ± 9.2 | 67.3 ± 14.3 | 51.8 ± 21.8 | 38.2 ± 18.9 | 70 ± 14.4 | 106.7 ± 37.4 |
| Bone | 4.8 ± 1.2 | 4.2 ± 1.7 | 3.0 ± 0.7 | 15.2 ± 6.9 | 15.2 ± 2.4 | 6.5 ± 1.9 |

FIG. 9

REAGENT FOR SITE-SELECTIVE BIOCONJUGATION OF PROTEINS OR ANTIBODIES

CROSS-REFERENCE TO RELATED APPLICATIONS

This application claims priority to, and is a non-provisional of U.S. Patent Applications 62/507,477 (filed May 17, 2017) and 62/634,385 (filed Feb. 23, 2018), the entirety of which are incorporated herein by reference.

STATEMENT OF FEDERALLY SPONSORED RESEARCH OR DEVELOPMENT

This invention was made with government support under grant numbers 4R00CA178205-02, R24CA3084 and P30CA08748 awarded by the National Institute of Health; G12MD007599 awarded by the National Institute on Minority Health and Health Disparities. The government has certain rights in the invention.

BACKGROUND OF THE INVENTION

The subject matter disclosed herein relates to site-selective biological radiolabels that are stable in vivo.

The ability of many biomolecules to selectively and specifically target cellular biomarkers has long been harnessed for both nuclear imaging and radiotherapy. This exploitation uses the ligation of a radioactive payload to the biomolecule. In the case of peptides and proteins, this is typically performed through the ligation of reactive, bifunctional probes to amino acids within the biomolecule, most often lysines. While controlling the site of this conjugation is fairly easy with small peptides—which rarely possess more than one or two copies of each amino acid—this becomes a much bigger problem with larger biomolecules. For example, most antibodies contain dozens of lysines distributed throughout their macromolecule structure. The indiscriminate attachment of a bifunctional chelator to these lysines can lead to the formation of thousands of different regioisomers. Not surprisingly, this so-called "random" approach to bioconjugation has low reproducibility and produces highly heterogeneous conjugates. In addition, this strategy can result in payloads being inadvertently grafted to bioactive sites in the biomolecule, rendering a portion of the conjugates inoperative.

To circumvent these issues, researchers have turned their attention to strategies allowing for better control over the site of the ligation reaction, known as "site-specific" bioconjugations. Conjugations to cysteine—a thiol-bearing amino acid present in small numbers in proteins—with maleimide-bearing probes have become a staple of this field and have been used extensively over the last three decades. The prevalence of this strategy is rooted mainly in its simplicity and efficiency. Many proteins contain disulfide bridges that can be easily reduced to form the reactive thiols, and the Michael addition between the maleimide and the sulhydryl group can be performed at physiological pH and room temperature, reliably leading to the formation of a succinimidyl thioether linkage within an hour (see FIG. 1).

While the ligation between thiols and maleimides represents an undeniable improvement over random conjugation methods, the reaction suffers from drawbacks as well. Indeed, maleimide-based conjugates display limited stability in physiological media because the succinimidyl thioether linkage can undergo a retro-Michael reaction that leads to the release of the payload or its exchange with other molecules containing free thiols (most often serum albumin, cysteine, and glutathione). Several studies focused on antibody-drug conjugates have reported on this phenomenon as well as the off-target uptake of payload that it creates. These studies have also been devoted to boosting the hydrolysis of the succinimyl moiety by modifying its vicinity, which ultimately prevents the thiol exchange and the off-target uptake of the drug. In the context of nuclear imaging and radiotherapy, this retro-Michael reaction can lead to the release of the radioactive payload and in vivo radiolabeling of endogeneous biomolecules through thiol exchange reactions (see FIG. 1). This "leakage" causes higher uptake in non-target tissues and lower uptake in target tissues, ultimately resulting in higher radiation doses to healthy tissues, reduced imaging contrast, and lower therapeutic ratios. Several alternatives which create more-stable linkages with thiols than maleimides have been used for the bioconjugation and radiolabeling of antibodies, most notably tosylates, bromo- and iodo-acetyls, and vinyl sulfones. However, each of these options has drawbacks as well, including lower reactivity with thiols as well as reactivity with other amino acids.

An article published in 2013 (Toda, N., Asano, S. & Barbas, C. F. (2013) Rapid, stable, chemoselective labeling of thiols with Julia-Kocieński-like reagents: A serum-stable alternative to maleimide-based protein conjugation. Angew. Chem. Int. Ed. 52, 12592-125%, hereafter "Toda et al.") holds particular promise in this area. In this work, the Barbas Laboratory described the creation of an oxadiazolyl methyl sulfone-based reagent that could selectively react with thiols at a rate comparable to maleimides and form more stable conjugates than those obtained with the latter (Scheme 1).

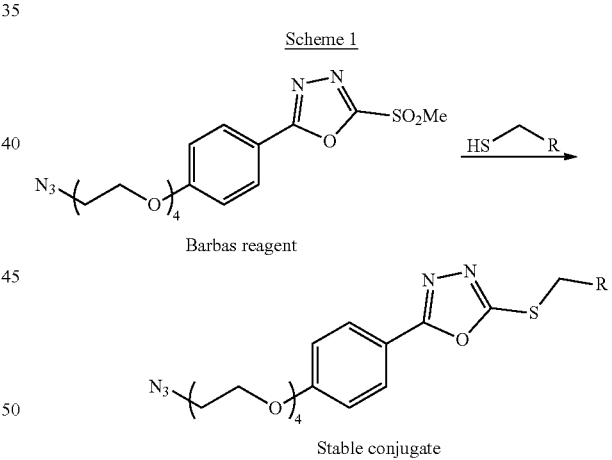

This reagent was used to label different THIOMABs—antibodies engineered to bear a free cysteine residues—with fluorescein, and these phenyloxadiazole-based conjugates displayed higher stability over time in serum than their maleimide-based cousins. Yet despite the benefits of this ligation over maleimide-thiol conjugations, this construct has scarcely been used since its publication. This is especially obvious in radiochemistry, in which only two reports describe the use of the reagent or its derivatives. In the first, Zhang et al. (Zhang, Q., Dall'Angelo, S., Fleming, I. N., Schweiger, L. F., Zanda, M. & O'Hagan, D. (2016) Last-step enzymatic [$^{18}$F]-fluorination of cysteine-tethered RGD peptides using modified Barbas linkers. *Chem.-Eur. J.* 22, 10998-11004) used this reagent along with other methylsulfone-oxadiazole derivatives to incorporate an azide moiety into an RGD peptide. In the second, a team in Switzerland designed an ¹⁸F-labeled prosthetic group based on this reagent which seemed to offer substantial advantages over traditional maleimide-based prosthetic groups for IF-labeling (Chiotellis, A., Sladojevich, F., Mu, L., Herde, A. M., Valverde, I. E., Tolmachev, V., Schibli, R., Ametamey, S. M. & Mindt, T. L. (2016) Novel chemoselective ¹⁸F-radiolabeling of thiol-containing biomolecules under mild aqueous conditions. *Chen Commun.* 52, 6083-6086).

The infrequent use of this reagent was somewhat surprising at first, especially since it is commercially available from Sigma-Aldrich. In three attempts at ordering, the product was discovered to contain complex mixtures of degradation products containing less than 15% of the desired compound. In light of these setbacks, synthesis of the reagent according to the published procedure was considered, but it appeared that this synthesis was far from trivial for radiochemical and molecular imaging laboratories that lack sophisticated organic chemistry equipment.

It would therefore be desirable to create an easily accessible phenyloxadiazole-based reagent for thiol conjugations that can be obtained through a robust route that could be carried out with basic organic chemistry equipment.

The discussion above is merely provided for general background information and is not intended to be used as an aid in determining the scope of the claimed subject matter.

BRIEF DESCRIPTION OF THE INVENTION

A label for an antibody or protein is described that is both site-selective and unusually stable in vivo. The label has a general formula given by

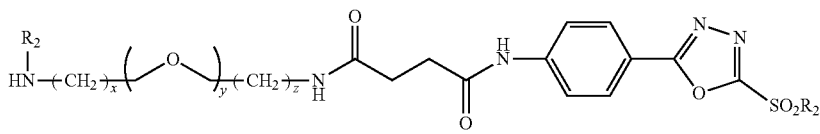

wherein $R_1$ is a metal chelator, fluorophore or a click-chemistry synthon. The disclosed compositions have surprising in vivo stability.

In a first embodiment, a label for an antibody or protein is provided. The label comprises a structure of

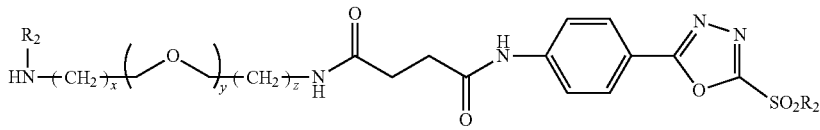

wherein: $R_1$ is a metal chelator or a click-chemistry synthon; $R_2$ is a methyl, ethyl or propyl; x is 1 or 2; y is 2 or 3 and z is 1 or 2.

In a second embodiment, a method for labeling a substrate is provided. The method comprises steps of: exposing a label to a substrate that comprises a cysteine residue, wherein the label comprises:

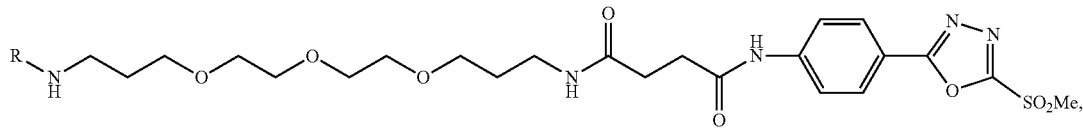

wherein R is a chelator or a click-chemistry synthon; and permitting the label to covalently bind to the cysteine residue of the substrate, thereby labeling the substrate.

In a third embodiment, a composition of matter is provided. The composition of matter consists of:

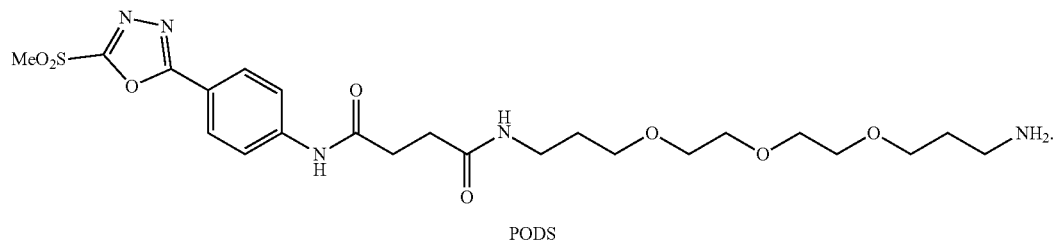

PODS

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 3A, 3B and 3C depict evolution of the reaction between PODS and model thiol-bearing biomolecules at various pH, wherein FIG. 3A depicts coupling of PODS and Boc-L-cysteine at pH 4.5; FIG. 3B depicts coupling of PODS and Boc-L-cysteine at pH 7.5; FIG. 3C depicts coupling of PODS and glutathione at pH 7.5;

FIGS. 6A, 6B and 6C illustrate the stability of the radiolabeled conjugates in human serum at 37° C. wherein FIG. 6A depicts the integrity of $^{89}$Zr-DFO-PODS-trast and $^{89}$Zr-DFO-mal-trast; FIG. 6B depicts the integrity of $^{89}$Zr-DFO-PODS-huA33 and $^{89}$Zr-DFO-mal-huA33; FIG. 6C depicts the integrity of $^{177}$Lu-CHX-A"-DTPA-PODS-trast and $^{177}$Lu-CHX-A"-DTPA-mal-trast;

FIGS. 7A, 6B, 7C and 7D depicts planar (FIG. 7A and FIG. 7B) and maximum intensity projection (FIG. 7C and FIG. 7D) PET images of athymic nude mice bearing A33-expressing SW1222 colorectal cancer xenografts (arrow) following the injection of $^{89}$Zr-DFO-PODS-huA33 and $^{89}$Zr-DFO-mal-huA33 (140 µCi, 60-65 µg), wherein the coronal slices intersect the center of the tumors;

FIG. 9 is a table depicts tumor-to-organ activity uptake ratios in nude mice for $^{89}$Zr-DFO-mal-huA33 and $^{89}$Zr-DFO-PODS-huA33 at various times;

DETAILED DESCRIPTION OF THE INVENTION

This disclosure describes the synthesis of two thiol-reactive bifunctional chelators for $^{89}$Zr and $^{177}$Lu based on a new, easy-to-make phenyloxadiazolyl methylsulfone reagent: PODS.

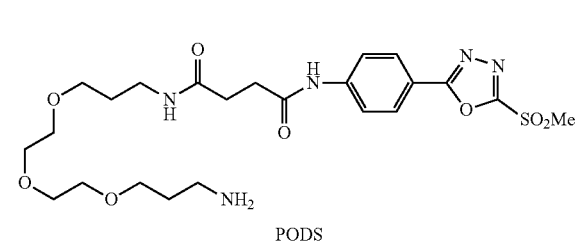

PODS

In one embodiment, PODS derivative is used that has a structure given by:

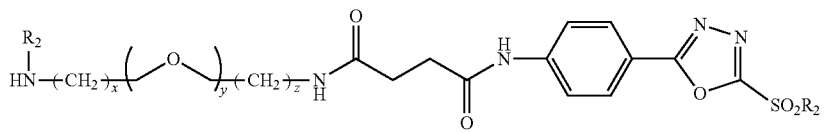

wherein: $R_1$ is a metal chelator, a fluorophore or a click-chemistry synthon; R is a methyl, ethyl or propyl; x is 1 or 2; y is 2 or 3 and z is 1 or 2.

Radioimmunoconjugates created using these novel bifunctional chelators displayed higher in vitro stability than their maleimide-derived cousins. More importantly, Positron emission tomography (PET) imaging in murine models of cancer revealed that a $^{89}$Zr-labeled radioimmunoconjugate created using a PODS-bearing bifunctional chelator produced significantly lower uptake in non-target tissues than its analogous maleimide-based counterpart.

The PODS reagent can be appended by numerous cargo through its terminal primary amine, allowing conjugation of that cargo to the biomolecule. For example, the bifunctional chelators PODS-DFO and PODS-ChxA"-DTPA allow for radiolabeling with the positron emitter Zirconium-89 (for ImmunoPET imaging) and the beta-emitter Lutetium-177 (for targeted radioimmunotherapy), respectively. A fluorophore cargo (e.g. fluorescein) can be attached to permit fluorescent imaging.

Conjugation to a Model Thiol

Figure 1:
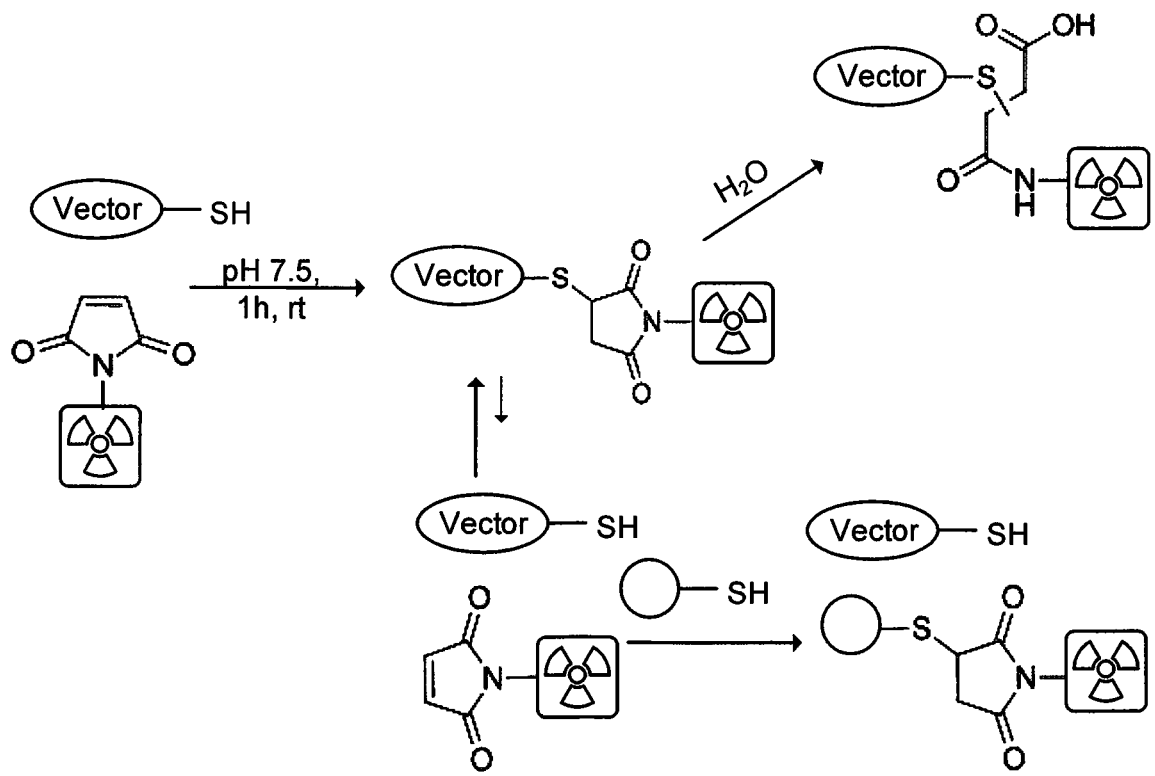
FIG. 1 is schematic of a Michael addition of a thiol-bearing biomolecule on a radionuclide-bearing maleimide to form a radiolabeled bioconjugate as well as the additional reactions that the radiolabeled construct can undergo in presence of endogenous thiol-bearing molecules.
Figure 2:
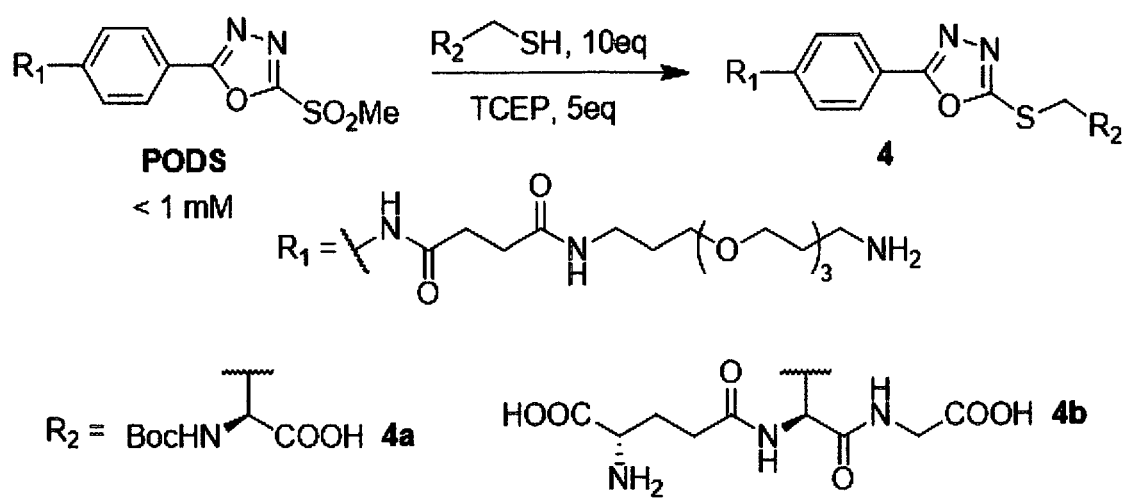
FIG. 2 is a schematic depicting the reaction of PODS with a model thiol.

In order to study the reactivity of PODS with thiols, Boc-L-cysteine was used as a model thiol in conjunction with the mild reducing agent tris(2-carboxyethyl)phosphine (TCEP), whose role was the reduction of any latent cystine species in solution (FIG. 2).

Figure 3A:
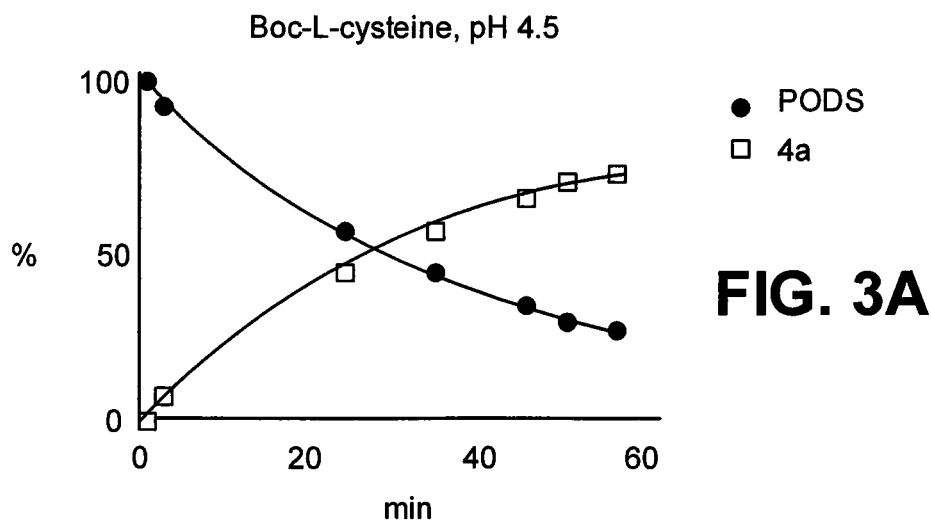
Figure 3B:
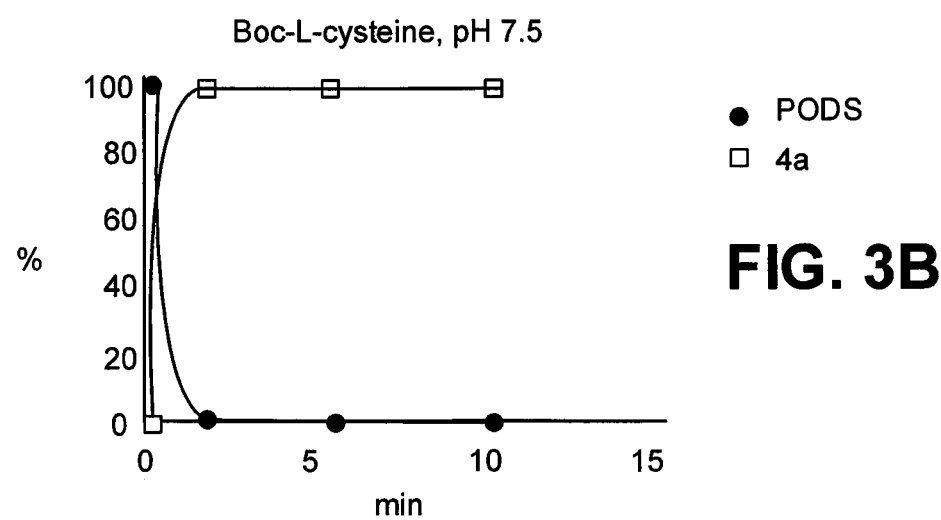
Figure 3C:
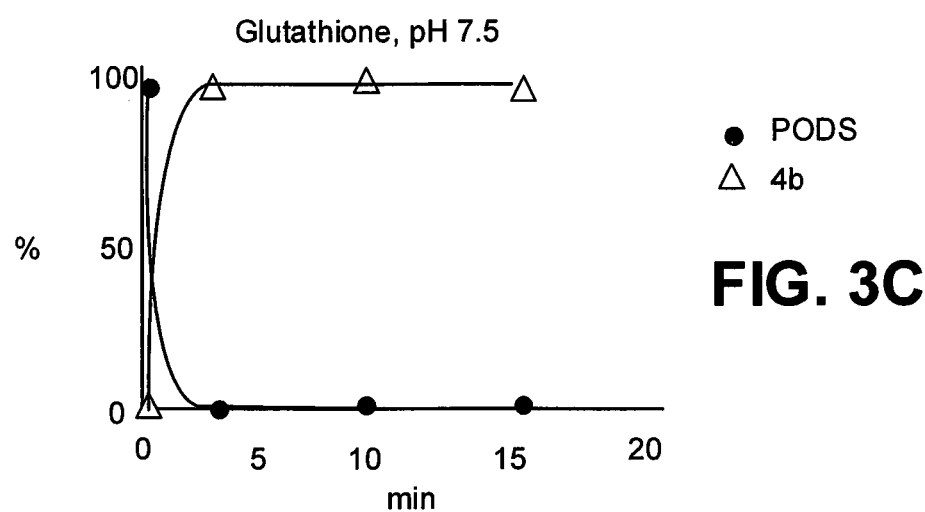

The reaction between PODS and Boc-L-cysteine was quantitative in less than 2 minutes at pH 7.5. See FIG. 3A, FIG. 3B and FIG. 3C. In a move toward a model closer to proteins and peptides, a tripeptide containing a central cysteine—glutathione—was reacted with PODS as well. Again, the conjugation reaction reached completion before the first measurement could be acquired (<3 min at pH 7.5).

Conjugation to a Model Antibody

Figure 5:
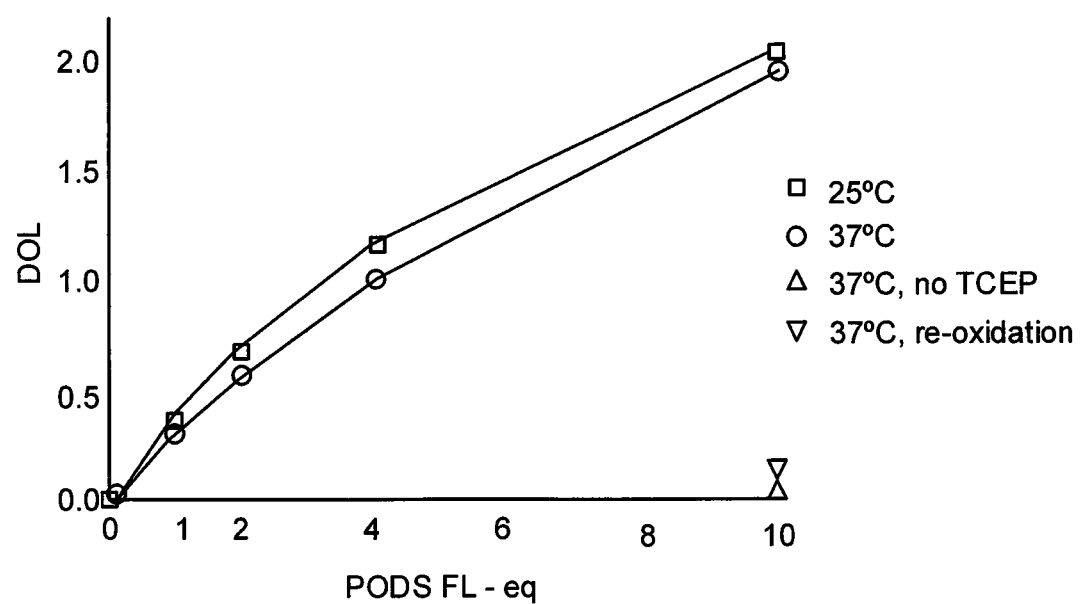
FIG. 5 is a plot of the degree of labeling (DOL) of the conjugates obtained after 2 h of reaction using different numbers of equivalent of PODS-FL under various conditions (10 equivalents of TCEP, unless specified otherwise)

Next, the utility of PODS for the site-specific modification of proteins was investigated. To this end, the well-characterized HER2-targeting humanized immunoglobulin trastuzumab was chosen as the model protein, and a fluorescent derivative of PODS (PODS-FL) was prepared via the reaction of PODS with fluorescein isothiocyanate. PODS-FL was conjugated with trastuzuab in the presence of TCEP, a mild reducing agent used to cleave the four inter-chain disulfide bonds within the immunoglobuhn (FIG. 2). Due to the presence of several thiol moieties available for the conjugation, this sub-class of modification is dubbed "site-selective", in opposition to the "site-specific" conjugations that yields highly homogeneous conjugates. Indeed, the grafting of cargoes on any of the eight available cysteines leads to the formation of several regioisomers. Although admittedly not perfect, site-selective conjugations still surpass by far the random conjugations of lysines, thanks to the controlled location of the conjugation sites—in the hinge region, far from the binding site—and their limited number. The number of fluorescein moieties present on the final conjugate was assessed using UV-Vis spectrophotometry. As expected, the degree of labeling (DOL) increased with the number of equivalents of PODS-FL in the reaction mixture (see FIG. 5), reaching 2.04±0.03 after two hours of incubation with 10 equivalents of PODS-FL. Surprisingly, the DOL was only minimally affected by the temperature of the reaction: similar results were obtained at 25° C. and 37° C. Even more importantly, the DOL of the immunoconjugates created via the incubation of 10 equivalents of PODS-FL with the antibody in the absence of TCEP or with the antibody following re-oxidization remained close to zero: 0.03±0.02 and 0.1±0.1, respectively. This last piece of data demonstrates the specificity of the reagent especially well.

In order to investigate the influence of antibody type on the efficacy of the conjugation reaction, several other antibodies—including human, humanized, chimeric, and murine constructs—were incubated with 10 equivalents of PODS-FL under the conditions described above (Table 1).

TABLE 1

Degree of labeling of different antibodies following conjugation with PODS-FL

| Antibody | Type | Constant region | Ratio FL:Ab |
|---|---|---|---|
| Human plasma IgG | Human | Human IgG | 2.1 ± 0.1 |
| Trastuzumab | Humanized | Human IgG1 | 2.0 ± 0.1 |
| huA33 | Humanized | Human IgG1 | 2.1 ± 0.1 |
| Cetuximab | Chimeric | Human IgG1 | 2.2 ± 0.1 |
| AR 9.6 | Murine | Murine IgG1 | 1.4 ± 0.1 |
| Mouse plasma IgG | Murine | Murine IgG | 1.5 ± 0.1 |

Intriguingly, while the DOL of the fully human, humanized, and chimeric immunoconjugates all remained slightly above 2, the number of fluorophores per antibody dropped to 1.5 for the murine immunoglobulins. This difference may be due to dissimilarities in the regions surrounding the disulfide linkages in murine antibodies.

Synthesis of Bifunctional Chelators

Thiol-reactive bifunctional chelators were synthesized based on PODS. Zirconium-89 and lutetium-177 were chosen as the proof-of-concept radionuclides for this study. Other suitable radionuclides include actinium-225, indium-111, gallium-68, copper-64, copper-67, aluminum-fluoride-18, yttrium-86, yttrium-90 and technetium-99. Over the last decade, $^{89}$Zr has become an essential nuclide for immuno-PET, and $^{177}$Lu is a β-emitting nuclide of growing interest for radioimmunotherapy. Accordingly, PODS was modified with desferrioxamine (DFO) and CHX-A"-DTPA, the 'gold standard' chelators for $^{89}$Zr and $^{177}$Lu, respectively.

Figure 4:
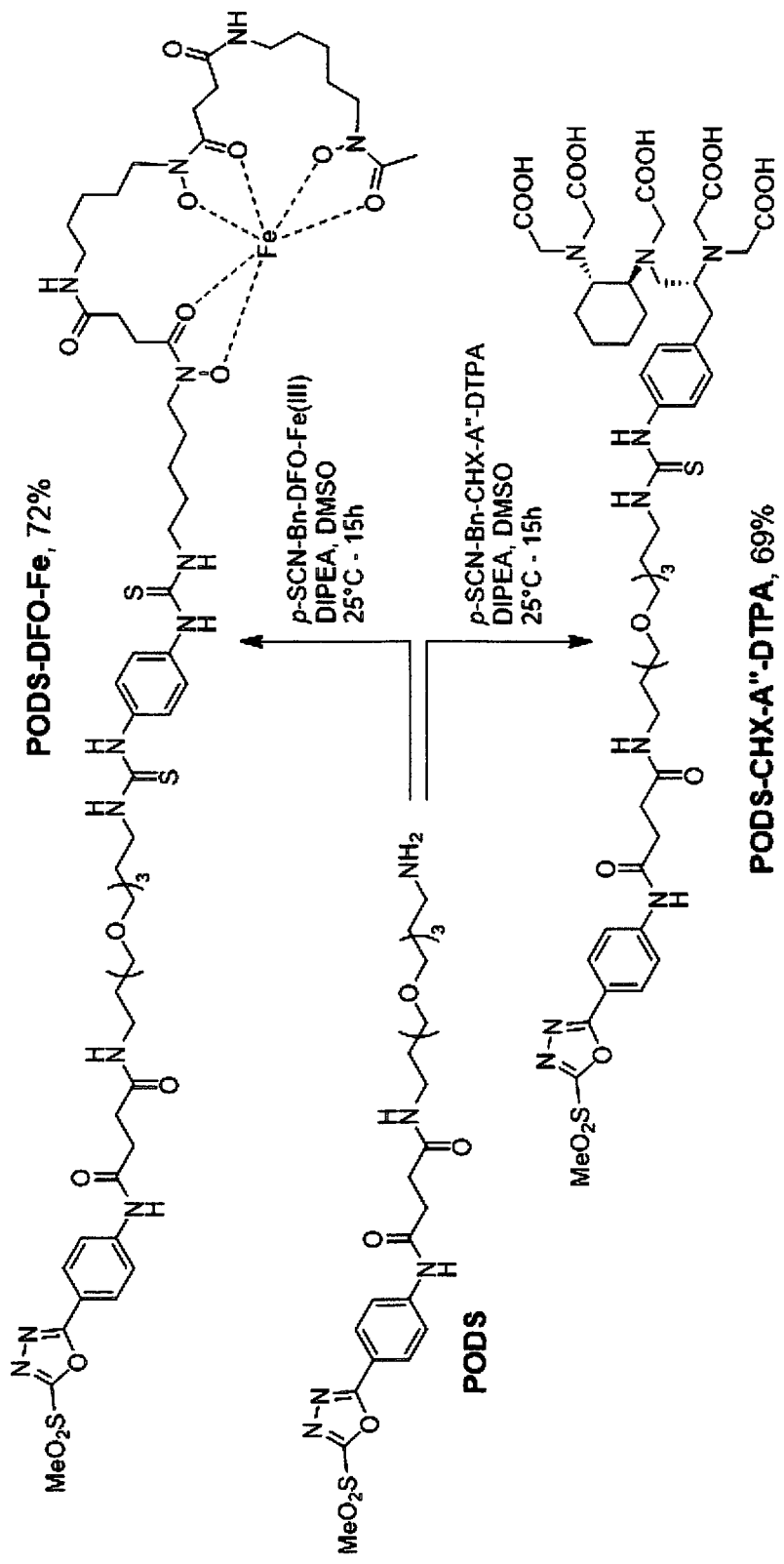
FIG. 4 depicts synthetic schemes for two PODS conjugates.

PODS-CHX-A"-DTPA was obtained in 69% yield via the reaction of PODS with an isothiocyanate-bearing derivative of CHX-A"-DTPA chelator in the presence of base (FIG. 4).

The synthesis PODS-DFO through a similarly straightforward approach turned out to be much trickier, as degradation products were commonly seen upon the analysis of the crude reaction mixture. Upon investigation, it became apparent that the hydroxylamines of the chelator react with PODS under basic conditions by substituting at methylsulfonyl position, causing the formation of undesired side products. To circumvent this, the hydroxylamine groups were protected via the coordination of iron. The resulting p-SCN- Bn-DFO-Fe was conjugated with PODS in presence of base, leading to the formation of PODS-DFO-Fe in good yield (72%) (FIG. 4). Pure PODS-DFO was obtained by removing the iron with an aqueous solution of oxalic acid 1M. However, free PODS-DFO underwent degradation in aqueous solution at pH >4.5, almost certainly due to the hydroxylamine-mediated reactions discussed above. Given the low reaction rate between PODS and thiols at this pH, unprotected PODS-DFO was deemed unsuitable for the modification of peptides and proteins.

Bioconjugation

The bifunctional chelators were then conjugated to a model antibody—trastuzumab—to produce DFO-PODS-trast and CHX-A"-DTPA-PODS-trast. A strategy similar to that developed by Verel et al. (Verel, I., Visser, G. W. M., Boellaard, K., Walsum, M. S., Snow, G. B. & Dongen, G. A. M. S. van. (2003) $^{89}$Zr Immuno-PET: comprehensive procedures for the production of $^{89}$Zr-labeled monoclonal antibodies. *J. Nucl. Med* 44, 1271-1281) was used to obtain the former: PODS-DFO-Fe was conjugated to the antibody, and the iron was removed thereafter. The ideal conditions for this decomplexation procedure were optimized for PODS-DFO-Fe using UV-Vis spectrophotometry, and 30 min of incubation at pH 4.5 and 25° C. in presence of EDTA—2.2 g/L—was found to lead to the removal of >95% of the iron from DFO. Informed by the experiments with PODS-FL, 10 equivalents of PODS-DFO-Fe and PODS-CHX-A"-DTPA were used with a goal of a final DOL of 2 chelators/mAb. Mass spectrometry confirmed that the immunoconjugates were indeed modified with PODS-DFO-Fe and PODS-CHX-A"-DTPA. However, the cleavage of the disulfide bonds resulted in the fragmentation of the antibody during MALDI-TOF which, in turn, rendered the accurate determination of the exact DOLs impossible. To facilitate in vitro comparisons, the maleimide-based counterparts of these two immunoconjugates—DFO-mal-trast and CHX-A"-DTPA-mal-trast—were also synthesized using identical reaction conditions.

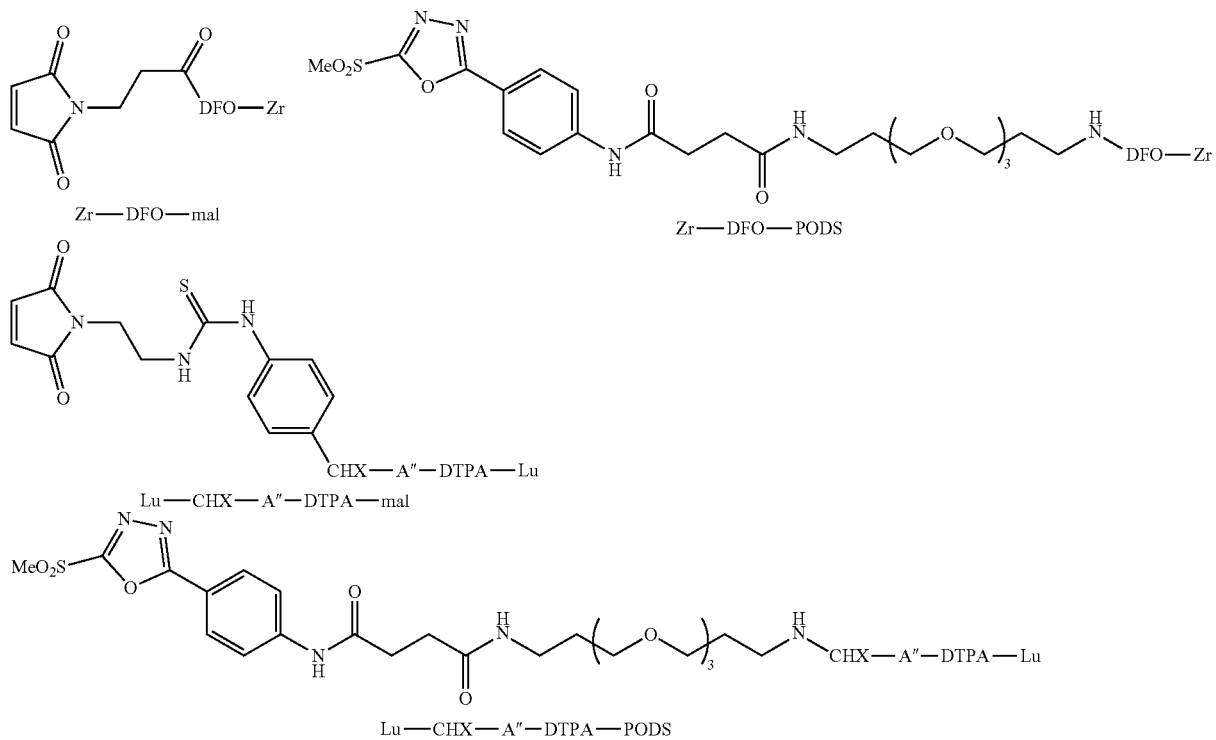

Radiolabeling and In Vitro Stability $^{89}$Zr-DFO-PODS-trast and $^{89}$Zr-DFO-mal-trast were each obtained in good yield, high purity, and similar specific activity—2.5±0.2 and 2.4±0.4 Ci/g, respectively—using standard $^{89}$Zr-radiolabeling protocols (Table 2). Likewise, typical $^{177}$Lu-labeling protocols were used to produce $^{177}$Lu-CHX-A"-DTPA-PODS-trast and $^{177}$Lu-CHX-A"-DTPA-mal-trast in high yield, high purity, and identical specific activities: 1.3±0.1 Ci/g.

TABLE 2

| Radiotracers | Specific activity - Ci/g | RCY - % | RCP - % |
|---|---|---|---|
| $^{177}$Lu-CHX-A"-DTPA-PODS-trast | 1.3 ± 0.1 | 97% | >99% |
| $^{177}$Lu-CHX-A"-DTPA-mal-trast | 1.3 ± 0.1 | 97% | >99% |
| $^{89}$Zr-DFO-PODS-trast | 2.5 ± 0.2 | 88% | >99% |
| $^{89}$Zr-DFO-mal-trast | 2.4 ± 0.4 | 85% | >99% |
| $^{89}$Zr-DFO-PODS-huA33 | 2.8 ± 0.4 | 95% | >99% |
| $^{89}$Zr-DFO-mal-huA33 | 2.8 ± 0.2 | 88% | >99% |

All four radioimmunoconjugates were incubated in human serum at 37° C. for one week, during which the integrity of the constructs was assessed using instant thin layer chromatography (ITLC). This trial clearly revealed that the PODS-based conjugates were more stable than their maleimide-based cousins. $^{89}$Zr-DFO-PODS-trast was 81±5% intact after seven days of incubation, whereas the integrity of $^{89}$Zr-DFO-mal-trast fell well below 70% by the same point: 63±12%. A similar difference—though admittedly of lesser magnitude—was obtained with the $^{177}$Lu-labeled immunoconjugates: $^{177}$Lu-CHX-A"-DTPA-PODS-trast and $^{177}$Lu-CHX-A"-DTPA-mal-trast were 82±1% and 76±2% intact, respectively, after 7 days. These difference in the stability of the maleimide- and PODS-based immunoconjugates are consistent with previously obtained data for antibody-fluorophore conjugates.

In Vivo Behavior

A different model system was chosen for a comparison of the in vivo behavior of $^{89}$Zr-DFO-PODS- and $^{89}$Zr-DFO-mal-based radioimmunoconjugates: huA33, a humanized antibody that targets the A33 antigen, a transmembrane glycoprotein expressed in more than 95% of colorectal cancers. There are two reasons for this switch. First, we wanted to interrogate the modularity of our PODS-based approach by validating our bioconjugation, stability, and in vitro results with a different antibody. Second, many HER2-expressing cell lines (e.g. BT474, SKOV3, etc.) exhibit irregular growth patterns in mice, resulting in heterogeneous tumors. In contrast, the two most often used A33 antigen-expressing cell lines—SW1222 and LS174T—grow extremely predictably in athymic nude mice, reliably forming xenografts with similar size and shape. Given that the goal of this phase of the investigation was to make comparisons between the in vivo behavior of PODS- and maleimide-based radioimmunoconjugates.

Figure 6A:
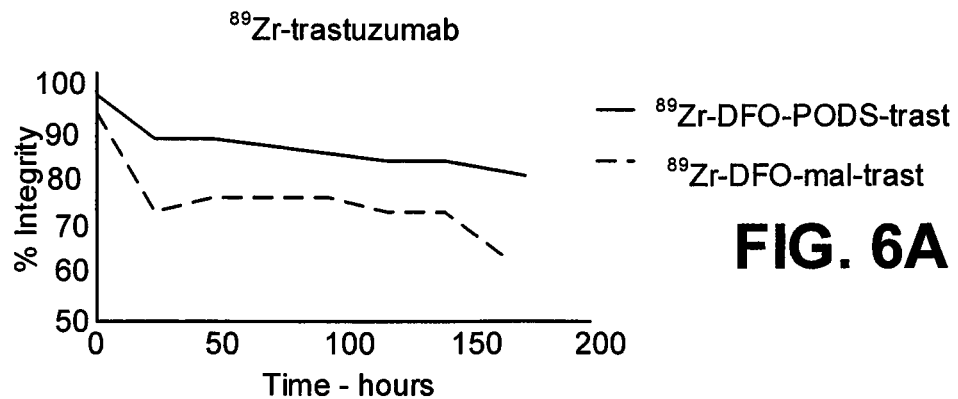
Figure 6B:
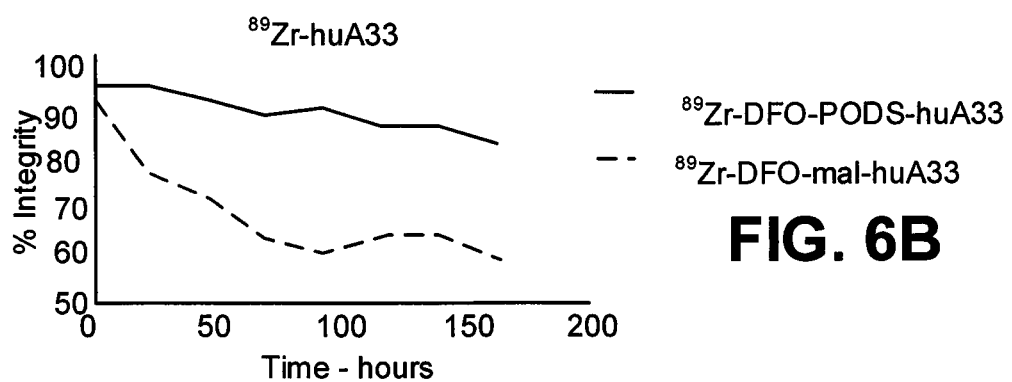
Figure 6C:
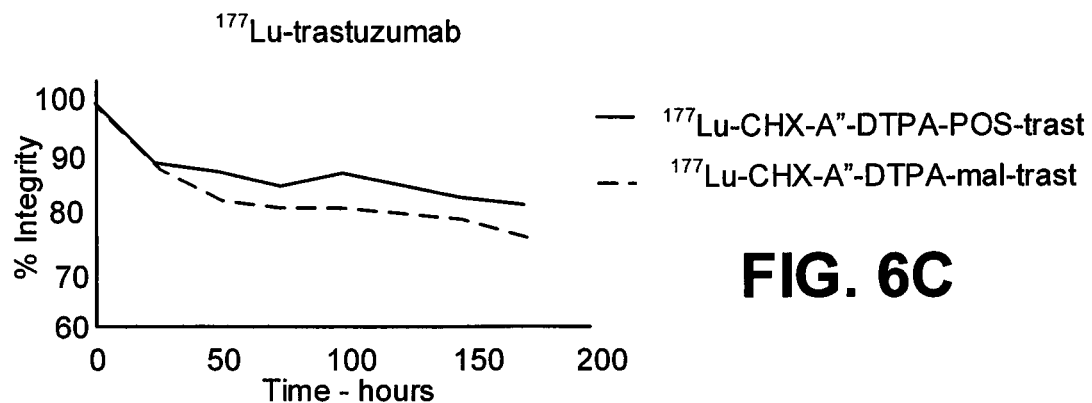
Figures 7C, 7D:
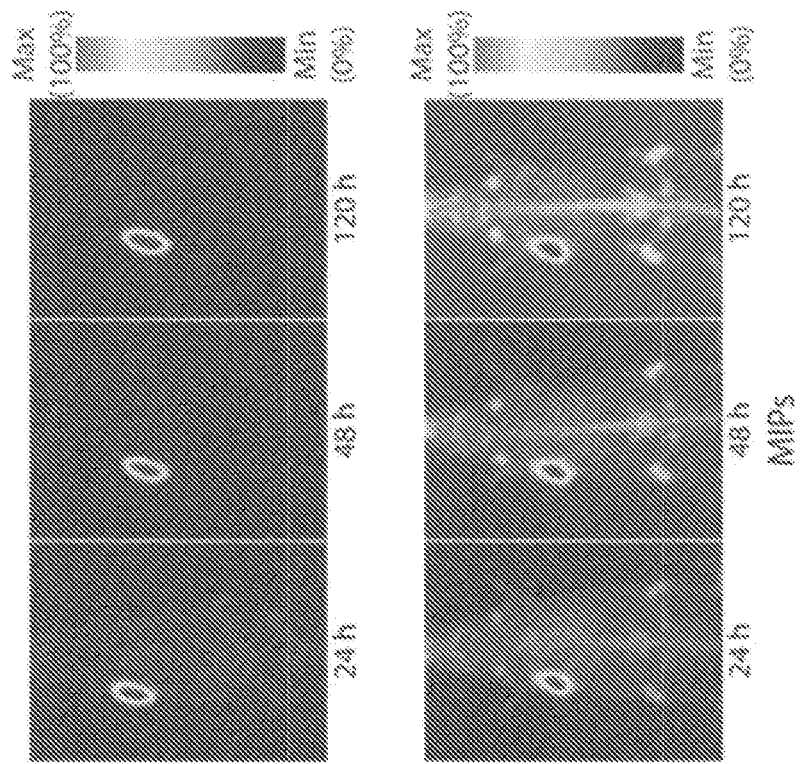
Figures 7A, 7B:
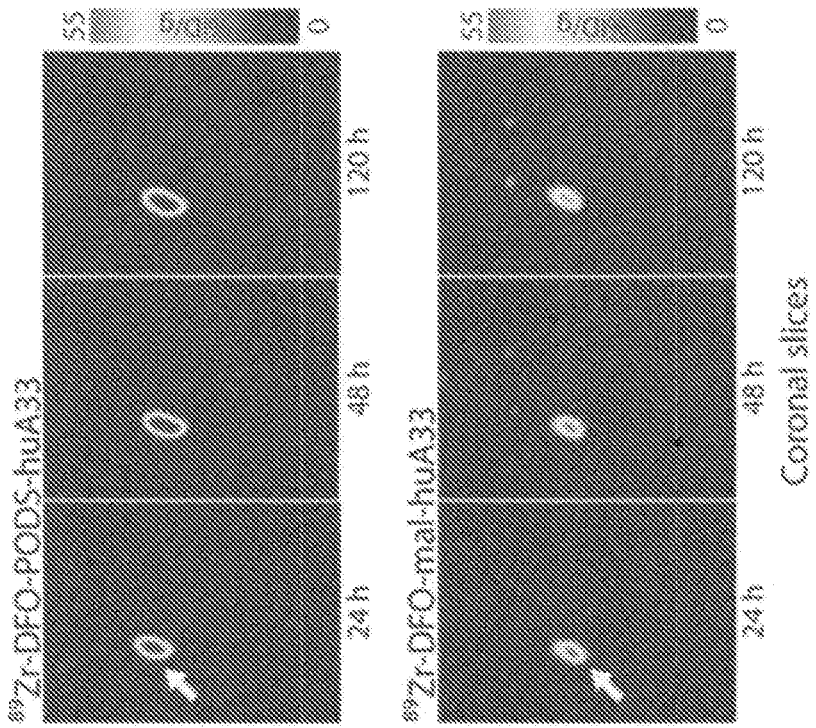

Using the procedures described elsewhere in this specification, DFO-PODS-huA33 and DFO-mal-huA33 were successfully synthesized and radiolabeled with $^{89}$Zr to produce $^{89}$Zr-DFO-PODS-huA33 and $^{89}$Zr-DFO-mal-huA33 in high yield, purity, and specific activity (2.8±0.4 and 2.8±0.2 Ci/g, respectively). The incubation of these radioimmunoconjugates in human serum for seven days at 37° C. yielded stability profiles similar to those obtained for the trastuzumab-based radioimmunoconjugates: after a week, $^{89}$Zr-DFO-PODS-huA33 remained 86±1% intact, while its maleimide-based cousin was only 61±5% intact (See FIG. 6A, FIG. 6B and FIG. 6C). The in vitro immunoreactivity of the two radioimmunoconjugates was determined via saturation binding assay with A33 antigen-expressing SW1222 human colorectal cancer cells. The immunoreactive fractions were similar for both constructs: 0.95±0.04 and 0.92±0.06 for $^{89}$Zr-DFO-PODS-huA33 and $^{89}$Zr-DFO-mal-huA33, respectively.

$^{89}$Zr-DFO-PODS-huA33 and $^{89}$Zr-DFO-mal-huA33 were injected into athymic mice bearing subcutaneous A33 antigen-expressing SW1222 human colorectal cancer xenografts. PET imaging revealed striking differences between the in vivo behavior of the two constructs (FIG. 7A, FIG. 7B, FIG. 7C and FIG. 7D). These disparities are particularly evident in the maximum intensity projections. $^{89}$Zr-DFO-PODS-huA33 displayed better tumor-to-background activity concentration ratios than the $^{89}$Zr-DFO-mal-huA33 at 24, 48, and 120 h post-injection. For $^{89}$Zr-DFO-mal-huA33, uptake in the bone was clearly visible as early as 24 h after administration and increased over time, and significant uptake in the kidneys and liver could also be observed. $^{89}$Zr-DFO-PODS-huA33, in contrast, produced much lower activity concentrations in each of these three tissues. The two constructs produced similar activity concentrations in the tumor: around 50-60% ID/g for each.

Figure 8:
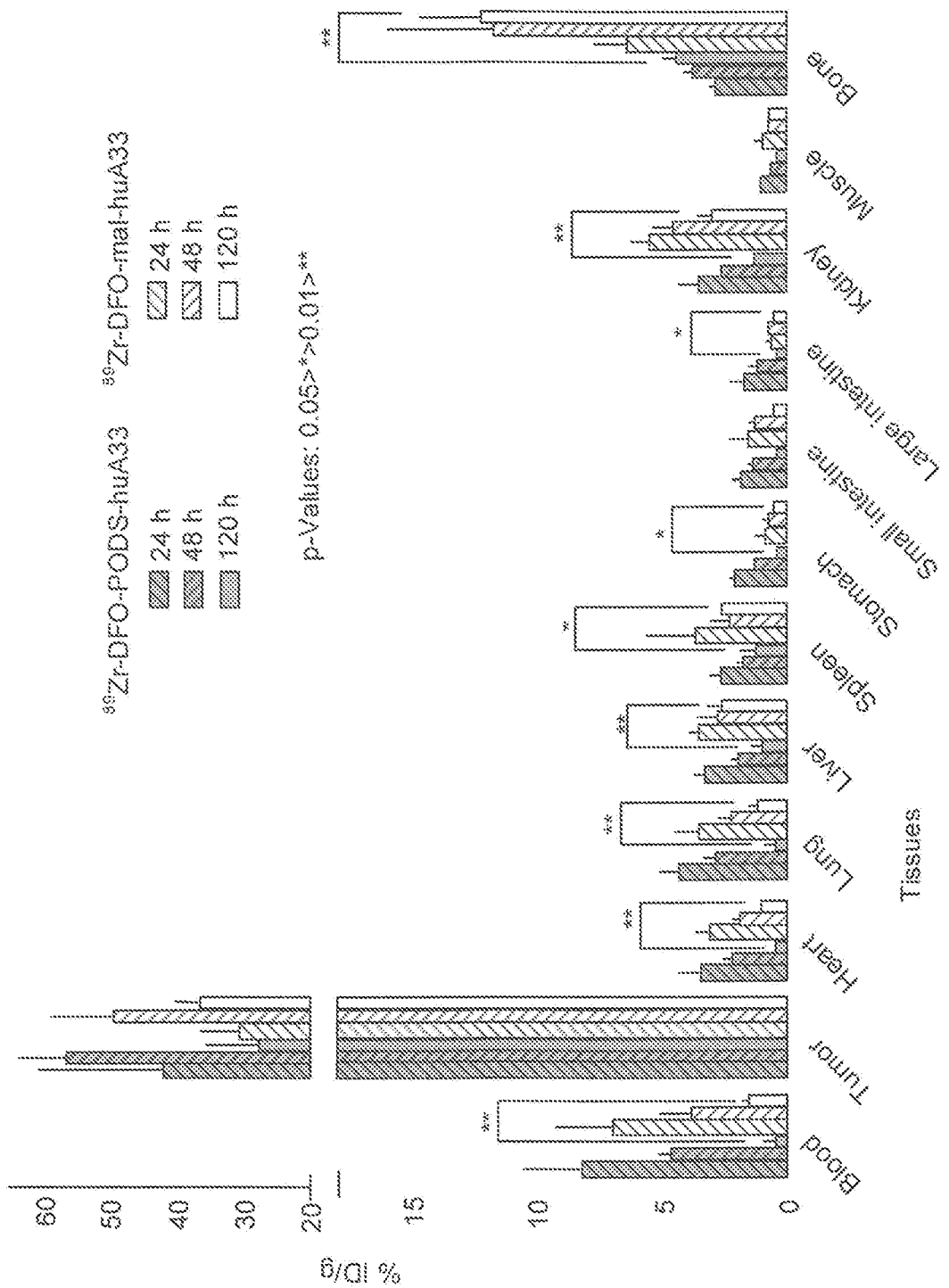
FIG. 8 is a graph showing biodistribution data after the administration of $^{89}$Zr-DFO-PODS-huA33 and $^{89}$Zr-DFO-mal-huA33 (30 µCi, 15-18 µg) to athymic nude mice bearing A33-expressing subcutaneous SW1222 human colorectal cancer xenografts.

The biodistribution data tells a similar story (FIG. 8). Most notably, $^{89}$Zr-DFO-mal-huA33 produces higher activity concentrations in the kidneys and bone than $^{89}$Zr-DFO-PODS-huA33. Similar tumoral activity concentrations were observed for the two radioimmunoconjugates; the decreases observed for both constructs between 48 h and 120 h post-injection were likely due to the growth of the tumors between the two timepoints. The efficient clearance of $^{89}$Zr-DFO-PODS-huA33 from healthy organs over the course of the study led to it producing lower uptake values in all non-target tissues—except the large intestine—at 120 h post-injection compared to $^{89}$Zr-DFO-mal-huA33. In contrast, $^{89}$Zr-DFO-mal-huA33 produced increasing activity concentrations in the bone over the course of the study and did not display any appreciable clearance from the liver and the spleen over 5 days. The tumor-to-organ activity concentration ratios obtained with $^{89}$Zr-DFO-PODS-huA33 are generally superior to those created by $^{89}$Zr-DFO-mal-huA33 at 120 h post-injection. FIG. 9 depicts tumor-to-organ activity uptake ratios for $^{89}$Zr-DFO-mal-huA33 and $^{89}$Zr-DFO-PODS-huA33 at 24 h, 48 h, and 120 h after injection in nude mice bearing SW1222 tumors.

The superior stability of the PODS-thiol linkage can explain these results. Indeed, the in vivo radiolabeling of endogenous thiol-bearing molecules and proteins caused by the retro-Michael reaction leads to off-target uptake of the radiometal and slower clearance from the non-target organs. Further, the metabolism of these radiolabeled endogenous biomolecules likely causes the release of $^{89}$Zr into the blood and translates into higher activity concentrations in the bone.

This disclosure described the synthesis of a new thiol-reactive phenyloxadiazolyl methylsulfone reagent—dubbed PODS—for the site-specific modification of peptides and proteins. This reagent was obtained in four steps with a global yield of 48% using a simple and straightforward synthetic route. PODS displayed rapid and selective reactivity with thiols and was successfully used to site-specifically modify a model antibody (trastuzumab) with a fluorophore. Bifumctional chelators were synthesized based on PODS: PODS-DFO (for $^{89}$Zr) and PODS-CHX-A"-DTPA (for $^{177}$Lu). Both of these constructs were used successfully for the site-specific modification and radiolabeling of trastuzumab, and $^{89}$Zr- and $^{177}$Lu-labeled radioimmunoconjugates based on PODS proved more stable in vitro than their maleimide-based analogs. Finally, the in vivo behavior of $^{89}$Zr-DFO-PODS-huA33 was compared to $^{89}$Zr-DFO-mal-huA33 in a murine model of human colorectal cancer, and the former was clearly revealed to be superior, especially for imaging with long delay (>48 h p.i.). Given the current practices for immunoPET in the clinic, where imaging 72-144 h after administration is commonplace, the use of PODS-based rather than maleimide-based radiotracers could make a significant difference in human patient imaging. Similarly, the higher stability of the $^{177}$Lu-labeled conjugate based on PODS could be greatly beneficial to radioimmunotherapy, leading to conjugates with higher therapeutic indexes by limiting the toxicity to healthy organs.

While this study has focused on the modification of IgGs, PODS-based reagents hold equal promise for the site-specific modification of cysteine-bearing antibody fragments, peptides, and proteins as well. In addition, bifunctional chelators similar to the ones described in this report could be created to accommodate virtually any radiometal, as amine-reactive derivatives of a wide range of chelators are currently commercially available. Ultimately, we sincerely hope that this work—and especially the simple and straightfoward chemistry that we have used here—will help promote the use of phenyloxadiozolyl reagents for thiol-based conjugations across a wide variety of disciplines and encourage researchers to move from maleimides to more reliable and more stable alternatives.

More specifically, the tumor-to-organ activity concentration ratios for the four organs with the highest uptake—liver, spleen, kidney and bone—are nearly double for $^{89}$Zr-DFO-PODS-huA33 compared to $^{89}$Zr-DFO-mal-huA33: 24.4±8.5 to 13.6±2.4 (tumor-to-liver), 23.2±13.4 and 14.9±1.6 (tumor-to-spleen), 19.4±5.2 and 12.0±12.3 (tumor-to-kidney), and 6.5±1.9 and 3.0±0.7 (tumor-to-bone). Indeed, the only organ for which the activity concentration ratio is lower for $^{89}$Zr-DFO-PODS-huA33 compared to $^{89}$Zr-DFO-mal-huA33 is the large intestine: 67±18 and 132±30, respectively.

Figure 10:
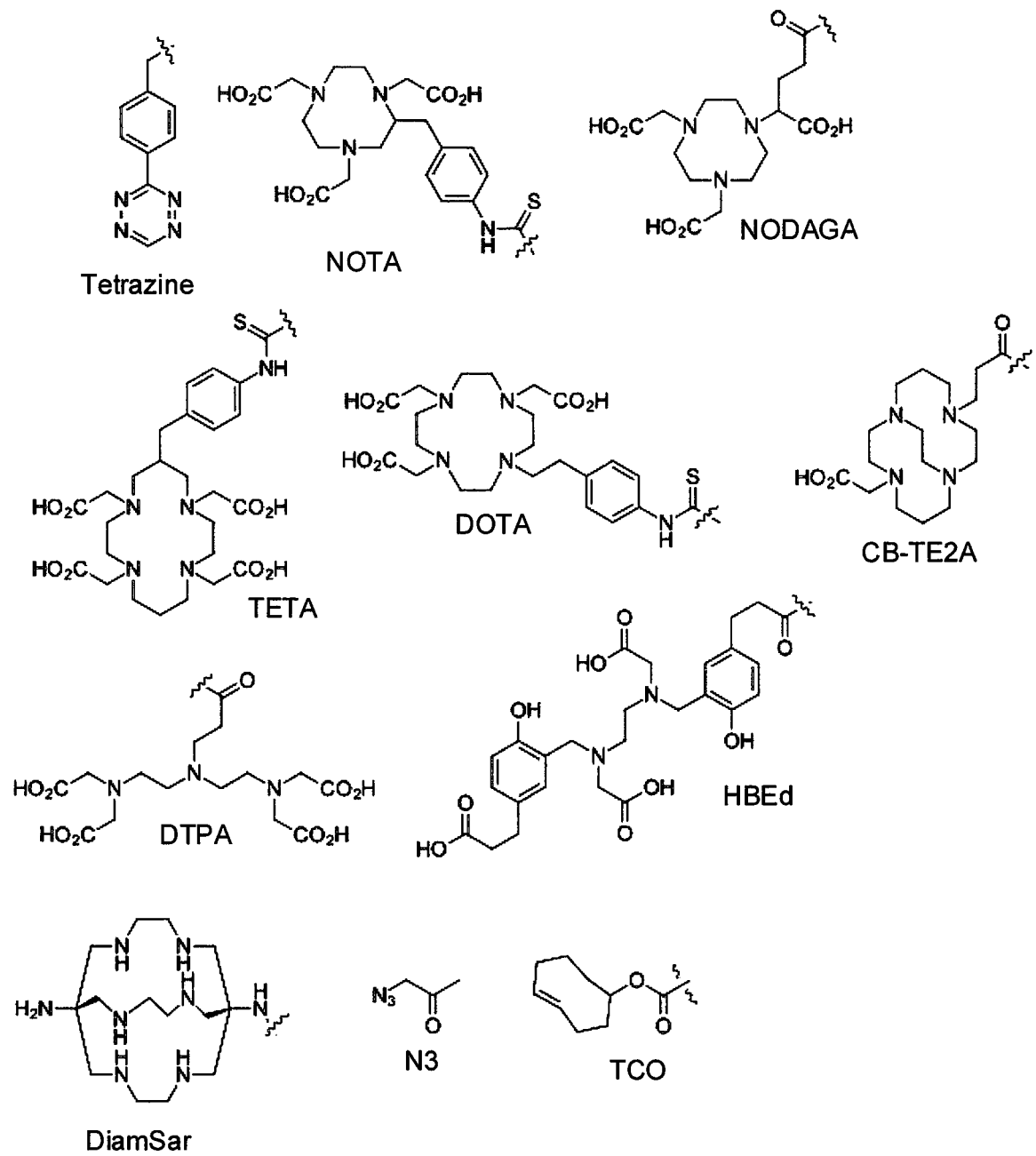
FIG. 10 depicts various tags that may be used in conjunction with PODS.

In other embodiments, other tags are used. Examples of such tags are illustrated in FIG. 10. TCO and N3 are examples of click-chemistry synthons. Metal chelators include tetrazine, 1,4,7-triazacyclononane-N,N',N''-triacetic acid (NOTA), 1,4,7-triazacyclononane,1-glutaric acid-4,7-acetic acid (NODAGA), 1,4,8,11-tetraazacyclotetradecane-N,N',N'',N'''-tetraacetic acid (TETA), 1,4,7,10-Tetraazacyclododecane-1,4,7,10-tetraacetic acid (DOTA), 1,4,8,11-Tetraazabicyclo[6.6.2]hexadecane-4,11-diacetic acid (CB-TE2A), diethylenetriaminepentaacetic acid (DTPA), hydroxybenzyl ethylenediamine (HBEd), and 1,8-Diamino-3,6,10,13,16,19-hexaazabicyclo[6,6,6]-eicosane (DiamSar).

Experimental Procedures

Figure 11:
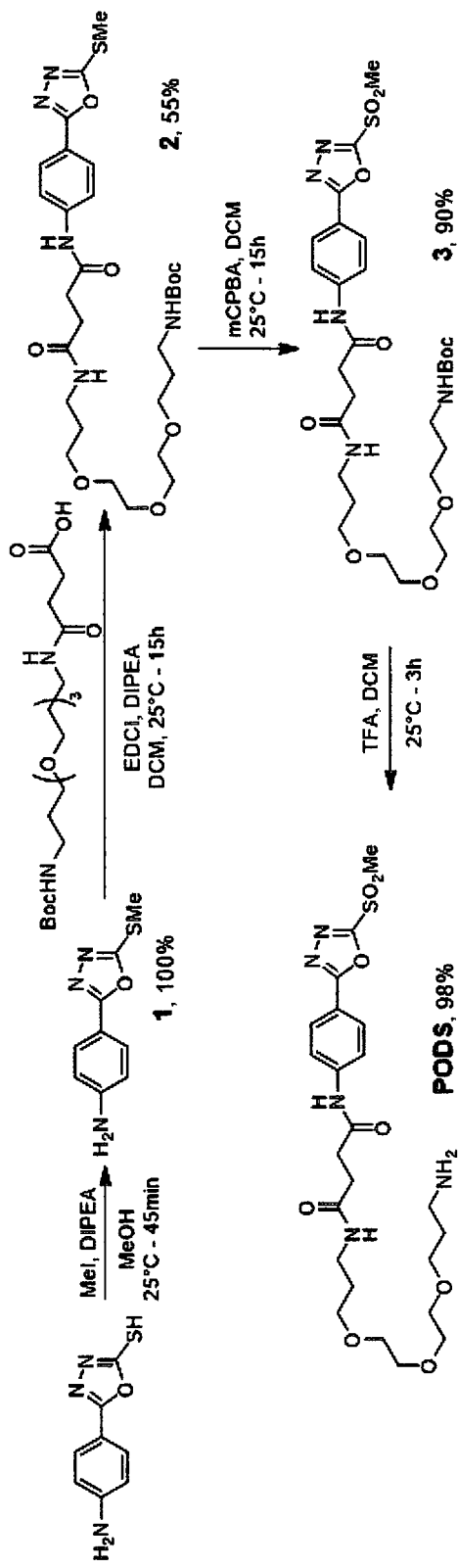
FIG. 11 depicts a depict synthetic scheme for forming PODS.

The disclosed phenyloxadiazolyl methyl sulfone derivative—dubbed 'PODS'—was obtained in four steps with a global yield of 48% (FIG. 11).

All intermediates were obtained in >95% purity using minimal equipment and simple procedures without chromatographic purifications. The methyl thioether 1 was

Synthesis of 4-(5-(methylthio)-1,3,4-oxadiazol-2-yl) aniline (1)

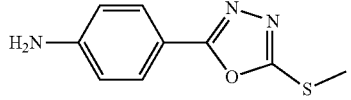

In a glass vessel protected from light with aluminium foil, 5-(4-aminophenyl)-1,3,4-oxadiazole-2-thiol (100 mg; 0.517 mmol; 1 eq.) was dissolved in 3 mL of methanol, and diisopropylethylamine (DIPEA; 360 μL; 2.07 mmol; 4 eq.) was added to the solution. The mixture was stirred at room temperature for 10 minutes before the slow addition of iodomethane (32 μL; 0.517 mmol; 1 eq.). After 45 minutes, the solvent was removed under reduced pressure. The white solid was dissolved in 3 mL of ethyl acetate and washed with a 0.1 M solution of sodium carbonate and then washed with water until reaching pH 7. The organic phase was dried over MgSO$_4$ before the evaporation of the volatiles under reduced pressure, ultimately affording white needles (107 mg; yield: 100%). Because of its slight light-sensitiveness, this compound was kept in foil-covered glass vials. TLC (Ethyl acetate:triethylamine, 9:1): Rf 0.65. $^1$H NMR (500 MHz, CDCl$_3$) 7.79 (2H, d, J=8.5 Hz), 6.72 (21, d, J=8.5 Hz), 4.04 (2H, br s), 2.75 (3H, s). $^{13}$C NMR (125 MHz, CDCl$_3$) 166.3, 163.7, 149.7, 128.5, 114.8, 113.5, 14.8. HRMS-ESI m/z Calcd for [C$_9$H$_9$N$_3$OS+H]$^+$: 208.0539; found: 208.0539; Δ: −0.80 ppm.

Synthesis of tert-Butyl (18-((4-(5-(methylthio)-1,3,4-oxadiazol-2-yl)phenyl)amino)-15,18-dioxo-4,7,10-trioxa-14-azaoctadecyl)carbamate (2)

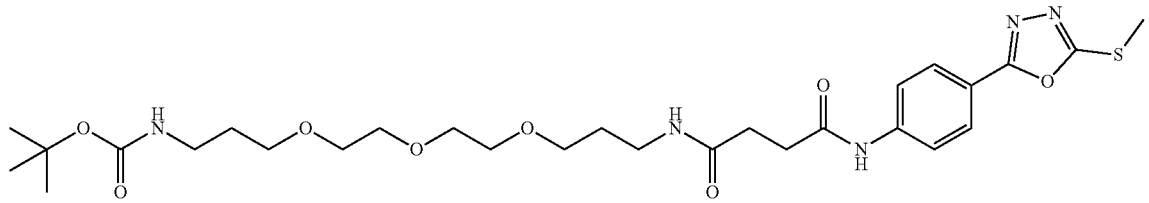 [SMILES: CSc1nnc(-c2ccc(NC(=O)CCC(=O)NCCCOCCOCCOCCCNC(=O)OC(C)(C)C)cc2)o1]

obtained quantitatively via the methylation of the thiol with methyl iodide; unfortunately, we were not able to replace the use of the toxic methyl iodide with any safer reagent. The coupling between 1 and the carboxylic acid-bearing PEG chain was performed using EDCI as a coupling agent. Overnight reaction at room temperature led to the complete consumption of the starting material but also the formation of degradation products. It was possible to separate 2 from the two unidentified impurities by precipitating it with a mixture of ethyl acetate and cyclohexane. The oxidation of 2 was performed using the peracid mCPBA. This lead to the formation of the methylsulfone 3 with a yield of 90%. Finally, PODS was obtained from 3 after the quantitative deprotection of the terminal amine using a solution of trifluoroacetic acid in dichloromethane. Solutions of PODS in DMSO were stable at room temperature and have been kept at room temperature for 5 months without any noticeable signs of degradation.

To a solution of N-Boc-N'-succinyl-4,7,10-trioxa-1,13-tridecanediamine (386.5 mg; 0.919 mmol; 1 eq.) in dichloromethane (3 mL) in a glass vessel protected from light with aluminum foil was added diisopropylethylamine (480 μL; 3 eq.) and N-ethyl-N'-(3-dimethylaminopropyl)carbodiimide hydrochloride (EDCI; MW=191.7 g/mol; 1.379 mmol; 1.5 eq.). To this solution was added 200 mg of 1 (0.965 mmol; 1.05 eq.). The reaction mixture was stirred at room temperature overnight. The mixture was then washed three times with 5 mL of an aqueous solution of 1 M hydrochloric acid. The organic phase was washed twice with 5 mL of an aqueous solution of 1 M Na$_2$CO$_3$ and then with water until pH neutral. The organic phase was dried on MgSO$_4$ and evaporated. The off-white solid residue was dissolved in 10 mL of ethyl acetate, and the target compound was precipitated by slow addition of 30 mL of cyclohexane. After filtration, the final product was obtained as a white powder (310 mg; yield: 55%). Because of its slight light-sensitiveness, this compound was kept in foil-covered glass vials. TLC (acetonitrile:water, 3:1): Rf 0.73. $^1$H NMR (500 MHz, CDCl$_3$) 9.68 (1H, s), 7.91 (2H, d, J=9.0 Hz), 7.71 (2H, d, J=8.5 Hz), 6.82 (1H, s), 4.99 (1H, s), 3.70-3.45 (121, m), 3.41 (2H, q, J=6.0 Hz), 3.20 (2H, q, J=6.5 Hz), 2.76 (3H, s), 2.71 (2H, m), 2.63 (2H, m), 1.80-1.70 (4H, m), 1.42 (9H, s). $^{13}$C NMR (125 MHz, CDCl$_3$) 172.6, 171.3, 165.8, 164.6, 156.2, 141.8, 127.7, 119.6, 118.6, 79.2, 70.6, 70.5, 70.3, 70.1, 69.6, 38.8, 38.5, 33.5, 31.6, 29.9, 28.6, 14.8. HRMS-ESI m/z Calcd for [C$_{28}$H$_{43}$N$_5$O$_8$S+Na]$^+$: 632.2725; found: 632.2722; Δ: 0.35 ppm.

Synthesis of tert-Butyl (18-((4-(5-(methylsulfonyl)-1,3,4-oxadiazol-2-yl)phenyl)amino)-15,18-dioxo-4,7,10-trioxa-14-azaoctadecyl)carbamate (3)

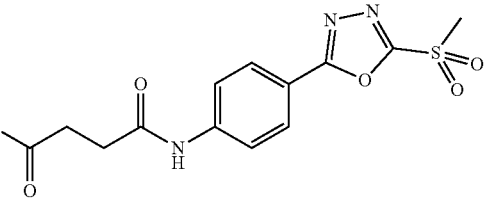

In a glass vessel protected from light with aluminium foil, 30 mg of 2 (0.049 mmol, 1 eq.) was dissolved in 4 mL of dichloromethane before the slow addition of 48.5 mg of m-chloroperbenzoic acid (70%, 0.197 mmol, 4 eq.). The reaction mixture was stirred at room temperature overnight. The resulting yellow mixture was washed three times with 8 mL of an aqueous 0.1 M solution of NaOH and then with water until the pH of the solution reached 7. The organic phase was dried over MgSO$_4$ and evaporated under reduced pressure to give a pale solid (28.5 mg, yield: 90%). TLC (acetonitrile): Rf 0.51. $^1$H NMR (500 MHz, CDCl$_3$) 9.99 (1H, s), 7.98 (2H, d, J=9.0 Hz), 7.75 (2H, d, J=8.5 Hz), 6.88 (1H, s), 4.99 (1H, s), 3.66-3.50 (151, m), 3.41 (2H, q, J=6.0 Hz), 3.20 (2H, q, J=6.5 Hz), 2.71 (2H, m), 2.65 (2H, m), 1.80-1.70 (4H, m), 1.43 (9H, s). $^{13}$C NMR (125 MHz, CDCl$_3$) 172.6, 171.5, 166.5, 161.6, 156.1, 143.4, 128.7, 119.6, 116.4, 79.1, 70.5, 70.4, 70.2, 70.0, 69.4, 43.0, 38.8, 38.4, 33.2, 31.3, 29.7, 28.4. HRMS-ESI m/z Calcd for [C$_{28}$H$_{43}$N$_5$O$_{10}$S+H]$^+$: 642.2803; found: 642.2797; Δ: 1.06 ppm.

Synthesis of N$^1$-(3-(2-(2-(3-Aminopropoxy)ethoxy)ethoxy)propyl)-N'-(4-(5-(methylsulfonyl)-1,3,4 oxadiazol-2-yl)phenyl)succinamide (PODS)

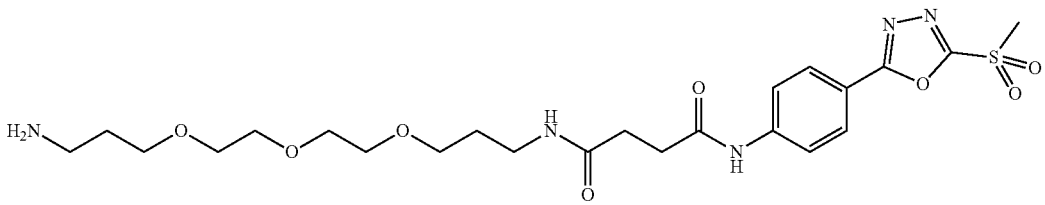 [SMILES: CS(=O)(=O)c1nnc(-c2ccc(NC(=O)CCC(=O)NCCCOCCOCCOCCCN)cc2)o1]

To a solution of 3 in dichloromethane (30.0 mg, 46.8 μmol; in 1.6 mL) was added trifluoroacetic acid (400 μL). The reaction mixture was stirred at room temperature for 3 hours, and the volatiles were then removed by evaporation under reduced pressure. The oily residue was dissolved in 7 mL of water and 4 mL of ethyl acetate. The aqueous phase was then washed twice with 4 mL of ethyl acetate. The aqueous layer was lyophilized to afford the final product as a white powder (25.0 mg, yield: 98%). TLC (acetonitrile:water, 3:1): Rf 0.38. $^1$H NMR (500 MHz, D$_2$O) 7.85 (2H, d, J=9.0 Hz), 7.55 (2H, d, J=8.5 Hz), 3.60-3.45 (15H, m), 3.45 (2H, t, J=6.5 Hz), 3.20 (2H, t, J=6.5 Hz), 3.04 (2H, t, J=7.0 Hz), 2.67 (2H, t, J=6.5 Hz), 2.54 (2H, t, J=6.5 Hz), 1.87 (2H, qt, J=6.5 Hz), 1.70 (2H, qt, J=6.5 Hz). $^{13}$C NMR (125 MHz, D$_2$O) 174.5, 173.2, 166.8, 161.4, 142.2, 128.6, 120.3, 116.6, 69.4, 69.4, 69.3, 69.2, 68.2, 68.2, 42.5, 37.6, 36.2, 31.9, 30.7, 28.2, 26.4. HRMS-ESI m/z Calcd. for [C$_{23}$H$_{35}$N$_5$O$_8$S+H]$^+$: 542.2279; found: 542.2281; Δ: -0.36 ppm.

Synthesis of PODS-FL

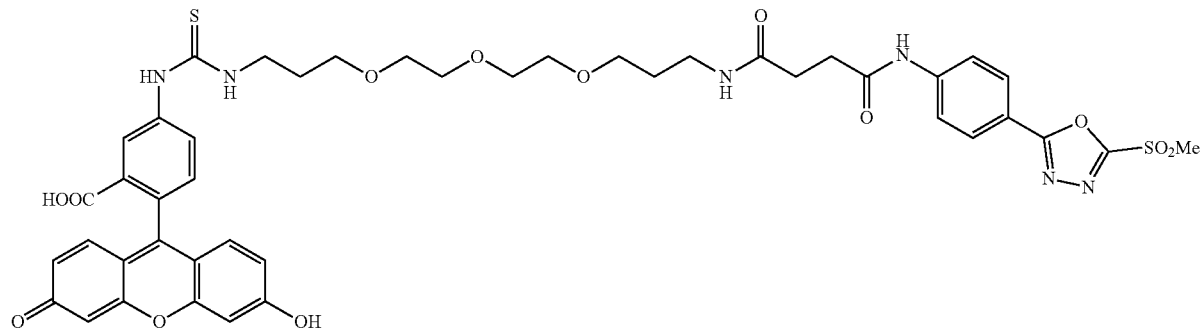 [SMILES: CS(=O)(=O)c1nnc(-c2ccc(NC(=O)CCC(=O)NCCCOCCOCCOCCCNC(=S)Nc3ccc(-c4c5ccc(=O)cc-5oc5cc(O)ccc45)c(C(=O)O)c3)cc2)o1]

To a solution of 6.0 mg of PODS in 600 uL of DMF (11.1 μmol, 1 eq.) was added 3.9 uL of DIPEA (22.2 μmol, 2 eq.) and 122 μL of a 0.1 M solution of fluorescein-isothyocyanate in DMSO (12.2 μmol, 1.1 eq.). The mixture was protected from light and let to react overnight at room temperature. The product was then purified by HPLC (gradient MeCN/H$_2$O+0.1% TFA, 0% MeCN to 100% in 30 min, R$_t$=22.5 min) to afford 3.8 mg of an orange powder (yield: 37%). HRMS-ESI m/z Calcd. for [C$_{44}$H$_{46}$N$_6$O$_{13}$S$_2$+H]$^+$: 931.2637; found: 931.2634; Δ: 0.27 ppm.

Synthesis of PODS-CHX-A″-DTPA

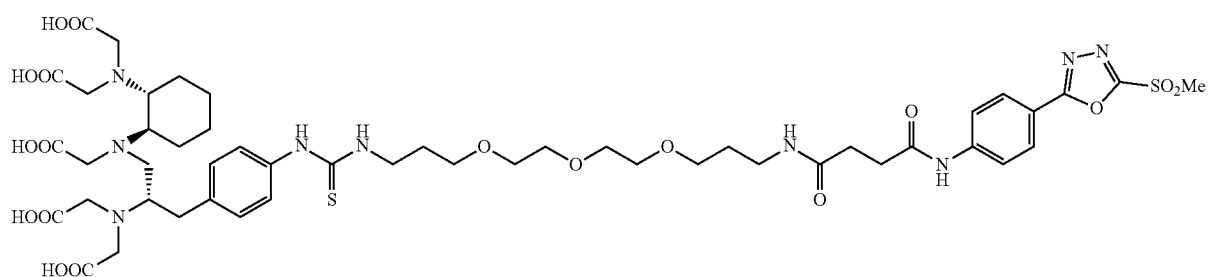 [SMILES: CS(=O)(=O)c1nnc(-c2ccc(NC(=O)CCC(=O)NCCCOCCOCCOCCCNC(=S)Nc3ccc(C[C@@H](CN(CC(=O)O)[C@@H]4CCCC[C@H]4N(CC(=O)O)CC(=O)O)N(CC(=O)O)CC(=O)O)cc3)cc2)o1]

To a solution of PODS (2.1 mg, 3.84 μmol, 1 eq.) in 200 μL of DMSO was added DIPEA (6.7 μL, 10 eq.). To this solution was added 3.0 mg of p-SCN-Bn-CHX-A″-DTPA-3HCl (4.25 μmol, 1.1 eq.; Macrocyclics, Inc.), and the mixture was stirred at room temperature overnight. The product was then purified by HPLC (gradient MeCN/H$_2$O+0.1% TFA, 0% MeCN to 100% in 25 min, R$_t$=19.5 min) to afford 3.0 mg of a white powder (yield: 69%). HRMS-ESI m/z Calcd. for [C$_{49}$H$_{69}$N$_9$O$_{18}$S$_2$+H]$^+$: 1136.4275; found: 1136.4273; Δ: 0.18 ppm.

Synthesis of PODS-DFO-Fe

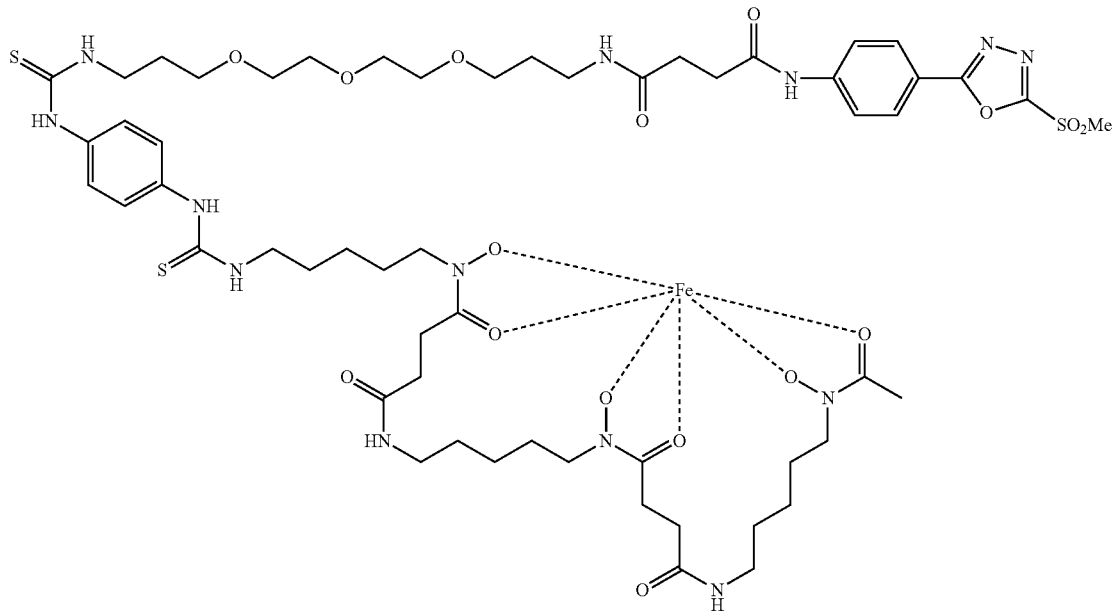

To a solution of p-SCN-Bn-DFO (5.0 mg, 6.65 mol, 1.2 eq.; Macrocyclics, Inc.) in 100 μL of DMSO was added 1.8 mg of FeCl$_3$ hexahydrate (6.65 μmol, 1.2 eq.). The resulting dark red solution was added to a solution of PODS (3.0 mg, 5.54 μmol, 1 eq.) in 100 μL of DMSO with DIPEA (4.83 μL, 5 eq.). The mixture was stirred at room temperature overnight. The product was then purified by HPLC (gradient MeCN/H$_2$O+0.1% TFA, 30% MeCN to 100% in 30 min, R$_t$=16.5 min) to afford 5.2 mg of a dark red solid (yield: 72%). HRMS-ESI m/z Calcd. for [C$_{56}$H$_{84}$FeN$_3$O$_6$S$_3$+H]$^+$: 1347.4745; found: 1347.4735; Δ: 0.74 ppm.

Preparation of mAb-PODS-FL conjugates: To a suspension of 200 μg of antibody in PBS pH 7.4 (1 mg/mL) was added 1.33 μL of a fresh TCEP solution (10 mM in water, 10 eq.) and the appropriate volume of a solution of PODS-FL (1 mM in DMSO). The reaction mixture was stirred on a thermomixer (25° C. or 37° C.) for 30 min, 2 h, or 24 h. The conjugate was then purified on a size exclusion column (Sephadex G-25 M, PD-10 column, GE Healthcare; dead volume=2.5 mL, eluted with 2 mL of PBS, pH 7.4) and concentrated using centrifugal filtration units with a 50,000 Da molecular weight cut off (AMICON™ Ultra 4 Centrifugal Filtration Units, Millipore Corp. Billerica, Mass.).

The fluorescein:mAb ratio was determined via UV-Vis spectrophotometry of the conjugate at 280 nm and 495 nm followed by calculation using the following equation:

$$A_{mAb} = A_{280} - (A_{495} \times CF)$$

$$DOL = \frac{[A_{max} \times MW_{mAb}]}{[[mAb] \times \varepsilon_{Dye495}]}$$

in which the correction factor (CF) for PODS-FL was 0.60 based on the absorbance spectrum of PODS-Fluoresceine in PBS, MW$_{mAb}$=150,000, $\varepsilon_{Dye495}$=75,000, and $\varepsilon_{280,\ mAb}$=210,000.

For the re-oxidation experiment, 200 μg of trastuzumab in PBS pH 7.4 (1 mg/mL) were first reduced with 1.33 μL of a fresh TCEP solution (10 mM in water, 10 eq). After 30 min of reaction, the reduced antibody was purified on a size exclusion column (Sephadex G-25 M, PD-10 column, GE Healthcare; dead volume=2.5 mL, eluted with 2 mL of PBS, pH 7.4) and concentrated using centrifugal filtration units with a 50,000 Da molecular weight cut off (AMICON™ Ultra 4 Centrifugal Filtration Units, Millipore Corp. Billerica, Mass.). This solution was then allowed to re-oxidize in open air for 10 min before the addition of 13.3 μL of a solution of PODS-FL (1 mM in DMSO). The reaction mixture was incubated for 2 h at 37° C. and then processed as described above.

Preparation of mAb-PODS-DFO conjugates: To a suspension of 1 mg of antibody in PBS pH 7.4 (1 mg/mL) was added 6.7 μL of a fresh TCEP solution (10 mM in water, 10 eq.) and 33 μL of a solution of PODS-DFO-Fe (2 mM in DMSO). The reaction mixture was stirred on a thermomixer at 2° C. for 2 hours. To this yellow solution was then added 100 μL of EDTA (tetrasodic salt, 25 g/L in water), and the pH was adjusted to 4.5 with 0.25 M H$_2$SO$_4$. The mixture was stirred at 25° C. for 30 min to yield a colorless solution, indicating the transchelation of the Fe(II) from the DFO. The conjugate was then purified on a size exclusion column (Sephadex G-25 M, PD-10 column, GE Healthcare; dead volume=2.5 mL, eluted with 2 mL of PBS, pH 7.4) and concentrated using centrifugal filtration units with a 50,000 Da molecular weight cut off (AMICON™ Ultra 4 Centrifugal Filtration Units, Millipore Corp. Billerica, Mass.).

Supporting Information

Additional supplemental data is available in provisional patent applications 62/507,477 (filed May 17, 2017) and 62/634,385 (filed Feb. 23, 2018), the contents of which are hereby incorporated by reference.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A label for an antibody or protein, the label comprising a structure of

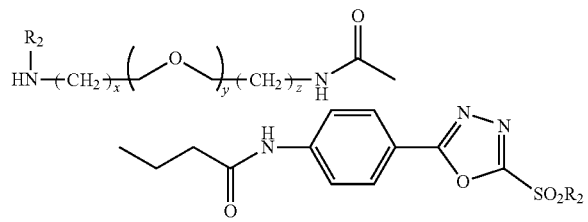

wherein:
$R_1$ is a metal chelator or a click-chemistry synthon;
$R_2$ is a methyl, ethyl or propyl;
x is 1 or 2;
y is 2 or 3 and
z is 1 or 2.

2. The label as recited in claim 1, wherein $R_1$ is a salt of a desferrioxamine (DFO) metal chelator wherein the salt comprises a positively charged metal ion.

3. The label as recited in claim 2, wherein the positively charged metal ion is selected from a group consisting of an iron ion and a Zr ion.

4. The label as recited in claim 2, wherein the positively charged metal ion is a Zr-89 ion.

5. The label as recited in claim 1, wherein $R_1$ is a salt of a [(R)-2-Amino-3-(4-isothiocyanatophenyl)propyl]-trans-(S,S)-cyclohexane-1,2-diamine-pentaacetic acid (CHX-A"-DTPA) wherein the salt comprises a positively charged metal ion.

6. The label as recited in claim 5, wherein the positively charged metal ion is a Lu ion.

7. The label as recited in claim 5, wherein the positively charged metal ion is a Lu-177 ion.

8. The label as recited in claim 1, wherein $R_1$ is salt of 1,4,7,10-Tetraazacyclododecane-1,4,7,10-tetraacetic acid (DOTA) and the salt comprises a positively charged metal ion.

9. The label as recited in claim 1, wherein $R_1$ is a salt of tetrazine and the salt comprises a positively charged metal ion.

10. The label as recited in claim 1, wherein $R_1$ is a salt of 1,4,8,11-tetraazacyclotetradecane-N, N', N", N'''-tetraacetic acid (TETA) and the salt comprises a positively charged metal ion.

11. The label as recited in claim 1, wherein $R_1$ is a salt of 1,4,7-triazacyclononane-N,N',N"-triacetic acid (NOTA) and the salt comprises a positively charged metal ion.

12. The label as recited in claim 1, wherein $R_1$ is a salt of 1,4,7-triazacyclononane,1-glutaric acid-4,7-acetic acid (NODAGA) and the salt comprises a positively charged metal ion.

13. The label as recited in claim 1, wherein $R_1$ is a salt of 1,4,8,11-Tetraazabicyclo[6.6.2]hexadecane-4,11-diacetic acid (CB-TE2A) and the salt comprises a positively charged metal ion.

14. The label as recited in claim 1, wherein $R_1$ is a salt of diethylenetriaminepentaacetic acid (DTPA) and the salt comprises a positively charged metal ion.

15. The label as recited in claim 1, wherein $R_1$ is a salt of hydroxybenzyl ethylenediamine (HBEd) and the salt comprises a positively charged metal ion.

16. The label as recited in claim 1, wherein $R_1$ is a salt of 1,8-Diamino-3,6,10,13,16,19-hexaazabicyclo[6,6,6]-eicosane (DiamSar) and the salt comprises a positively charged metal ion.

17. The label as recited in claim 1, wherein, $R_1$ is a metal chelator, $R_2$ is a methyl or an ethyl; x is 2; y is 3 and z is 2.

18. The label as recited in claim 1, wherein R is a click-chemistry synthon selected from N3 and TCO.

19. A method for labeling a substrate, the method comprises steps of:
exposing a label to a substrate that comprises a cysteine residue, wherein the label comprises:

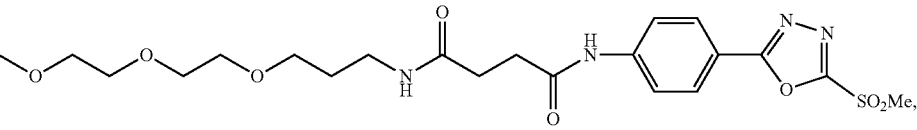

wherein R is a chelator or a click-chemistry synthon;
permitting the label to covalently bind to the cysteine residue of the substrate, thereby labeling the substrate.

20. A composition of matter consisting of:

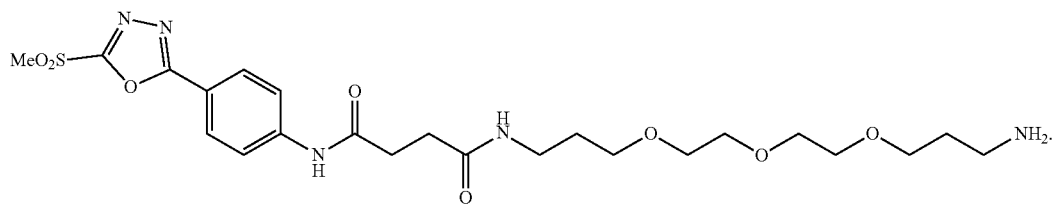

PODS

* * * * *

UNITED STATES PATENT AND TRADEMARK OFFICE
CERTIFICATE OF CORRECTION

PATENT NO. : 11,000,604 B2
APPLICATION NO. : 16/614073
DATED : May 11, 2021
INVENTOR(S) : Zeglis et al.

It is certified that error appears in the above-identified patent and that said Letters Patent is hereby corrected as shown below:

In the Claims

Column 21, Line 11, delete the chemical structure in Claim 1 and insert the following chemical structure:

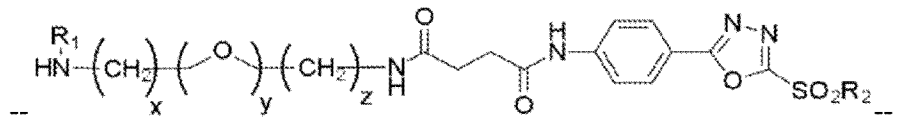

Column 22, Line 36, Claim 18 delete the text "R" and insert the text --R1--

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*